(12) United States Patent
Hosomi et al.

(10) Patent No.: US 9,121,051 B2
(45) Date of Patent: Sep. 1, 2015

(54) METHOD OF DETERMINING THE ABUNDANCE OF A TARGET NUCLEOTIDE SEQUENCE OF A GENE OF INTEREST

(71) Applicants: Toshiya Hosomi, Kyoto (JP); Moeko Ijuin, Kyoto (JP)

(72) Inventors: Toshiya Hosomi, Kyoto (JP); Moeko Ijuin, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 174 days.

(21) Appl. No.: 13/664,674

(22) Filed: Oct. 31, 2012

(65) Prior Publication Data

US 2013/0143212 A1 Jun. 6, 2013

Related U.S. Application Data

(63) Continuation of application No. PCT/JP2012/077916, filed on Oct. 29, 2012.

(60) Provisional application No. 61/553,572, filed on Oct. 31, 2011.

(51) Int. Cl.
*C12P 19/34* (2006.01)
*C12Q 1/68* (2006.01)

(52) U.S. Cl.
CPC .................................. *C12Q 1/6809* (2013.01)

(58) Field of Classification Search
CPC ........... C12Q 1/6809; C12Q 2525/161; C12Q 2527/107; C12Q 2527/143; C12Q 2537/143
USPC .............................................. 435/91.2, 91.21
See application file for complete search history.

(56) References Cited

U.S. PATENT DOCUMENTS

| | | | |
|---|---|---|---|
| 2006/0216737 A1* | 9/2006 | Bodeau et al. | ..................... 435/6 |
| 2010/0151448 A1 | 6/2010 | Zhang et al. | |
| 2011/0244460 A1 | 10/2011 | Hirai et al. | |
| 2011/0294676 A1* | 12/2011 | Cawthon | ........................... 506/7 |
| 2012/0202214 A1* | 8/2012 | Omi | ............................. 435/6.12 |

FOREIGN PATENT DOCUMENTS

| | | | |
|---|---|---|---|
| CN | 1496413 | A | 5/2004 |
| CN | 1629305 | A | 6/2005 |
| CN | 102076849 | A | 5/2011 |
| JP | 7-505053 | A | 6/1995 |
| JP | 2004-337124 | A | 12/2004 |
| JP | 2005-512577 | A | 5/2005 |
| JP | 2010-528592 | A | 8/2010 |
| JP | 2010-246419 | A | 11/2010 |
| JP | 2010-538614 | A | 12/2010 |
| JP | 2011-500063 | A | 1/2011 |
| JP | 2011-516069 | A | 5/2011 |
| JP | 2012-100628 | A | 5/2012 |
| WO | 2004/099439 | A1 | 11/2004 |
| WO | 2008/144841 | A1 | 12/2008 |
| WO | 2009/052547 | A1 | 4/2009 |
| WO | 2010/071147 | A1 | 6/2010 |
| WO | 2010/088288 | A2 | 8/2010 |
| WO | 2010/138460 | A1 | 12/2010 |
| WO | 2011/043220 | A1 | 4/2011 |

OTHER PUBLICATIONS

Hosono et al., "CYP2D6 Genotyping for Functional-Gene Dosage Analysis by Allele Copy Number Detection," Clinical Chemistry, 55: 1546-1554 (2009).
Kallioniemi et al., "ERBB2 Amplification in Breast Cancer Analyzed by Fluorescence in situ Hybridization," Proc. Natl. Acad. Sci., 89: 5321-5325 (1992).
Zhang et al., "Sensitive Detection of SARS Coronavirus RNA by a Novel Asymmetric Multiplex Nested RT-PCR Amplification Coupled with Oligonucleotide Microarray Hybridization," Methods in Molecular Medicine, 114: 59-78 (2005).
Metzler et al., "Asymmetric multiplex-polymerase chain reaction—a high throughput method for detection and sequencing genomic fusions sites in t(4;11)," British Journal of Haematology, 124: 47-54 (2004).
Zhu et al., "Use of a DNA Microarray for Simultaneous Detection of Antibiotic Resistance Genes among Staphylococcal Clinical Isolates," Journal of Clinical Microbiology, 45: 3514-3521 (2007).
Shimizu et al., "Universal Fluorescent Labeling (UFL) Method for Automated Microsatellite Analysis," DNA Research, 9: 173-178 (2002).
Oetting et al., "Multiplexed short tandem repeat polymorphisms of the Weber 8A set of markers using tailed primers and infrared fluorescence detection," Electrophoresis, 19: 3079-3083 (1998).
Notice of Reasons for Rejection (Non-Final) issued in corresponding Japanese Patent Application No. 2013-509391 dated May 28, 2013.
Notice of Reasons for Rejection (Final) issued in corresponding Japanese Patent Application No. 2013-509391 dated Oct. 22, 2013.
Decision of Refusal issued in corresponding Japanese Patent Application No. 2013-509391 dated Feb. 12, 2014.
Decision to Grant a Patent issued in corresponding Japanese Patent Application No. 2013-509391 dated Jun. 10, 2014.
Office Action issued in corresponding Chinese Patent Application No. 201280053730.7 dated Mar. 25, 2015.
Rudi et al., "A novel multiplex quantitative DNA array based PCR (MQDA-PCR) for quantification of transgenic maize in food and feed," Nucleic Acids Research, 31: e62 (2003).
Heide et al., "Determination of eight genetically modified maize events by quantitative, multiplex PCR and fluorescence capillary gel electrophoresis," European Food Research and Technology, 227: 1125-1137 (2008).
Extended European Search Report issued in corresponding European Patent Application No. 12844982.4 dated Mar. 31, 2015.

* cited by examiner

*Primary Examiner* — Cynthia B Wilder
(74) *Attorney, Agent, or Firm* — Morgan, Lewis & Bockius LLP

(57) ABSTRACT

The disclosure relates to a method of measuring gene abundance, including obtaining at least two types of amplification product, each of which contains a single additional base sequence and corresponds to each of at least two genes, by amplifying, in one reaction solution, nucleic acids encoding the at least two genes, whose abundances in nucleic acids contained in a subject sample may be different, using a first primer set, which includes at least two types of first primer, each of which is capable of introducing the single additional base sequence to a resulting amplification product and corresponds to each of the at least two genes, and a second primer for amplifying a nucleic acid containing the single additional base sequence; and determining the abundances of the at least two genes based on detected signals corresponding to the abundances of the at least two types of amplification product.

24 Claims, 5 Drawing Sheets

SEQUENCE LISTING

```
<160> NUMBER OF SEQ ID NOS: 25

<210> SEQ ID NO 1
<211> LENGTH: 300
<212> TYPE: DNA
<213> ORGANISM: Homo sapiens

<400> SEQUENCE: 1
tgagaacctg tgcatagtgg tggctgacct gttctctgcc gggatggtga ccacctcgac    60
cacgctggcc tggggcctcc tgctcatgat cctacatccg gatgtgcagc gtgagcccat   120
ctgggaaaca gtgcaggggc cgagggagga agggtacagg cggggggccca tgaactttgc   180 tgggacaccc ggggctccaa gcacaggctt gaccaggatc ctgtaagcct gacctcctcc   240
aacataggag gcaagaagga gtgtcagggc cggacccct gggtgctgac ccattgtggg    300

<210> SEQ ID NO 2
<211> LENGTH: 300
<212> TYPE: DNA
<213> ORGANISM: Homo sapiens

<400> SEQUENCE: 2
cctatgacaa aaatatttta atacatgtaa tataacattt tactgtaatt attgaaatct    60
gttcatttgt gggtggtttt ggatttttt tttaataggg gagttgctgg aagccatcaa    120
acgtgacttt ggttcctttg acaagttaa ggagaagctg acggctgcat ctgttggtgt    180
ccaaggctca ggttggggtt ggcttggttt caataaggaa cggggacact tacaaattgc    240
tgcttgtcca aatcaggatc cactgcaagg aacaacaggt tagatttaaa aattgtgatt    300

<210> SEQ ID NO 3
<211> LENGTH: 45
<212> TYPE: DNA
<213> ORGANISM: Artificial
<220> FEATURE:
<223> OTHER INFORMATION: 2D6-P3F4-Int6r-F1; primer

<400> SEQUENCE: 3
```

```
cgctgtagtc gaagacgatg tttacgtgag cccatctggg aaaca        45
```

<210> SEQ ID NO 4
<211> LENGTH: 21
<212> TYPE: DNA
<213> ORGANISM: Artificial
<220> FEATURE:
<223> OTHER INFORMATION: 2D6-Int6f-R1; primer

<400> SEQUENCE: 4

```
ggtgtcccag caaagttcat g                                  21
```

<210> SEQ ID NO 5
<211> LENGTH: 18
<212> TYPE: DNA
<213> ORGANISM: Artificial
<220> FEATURE:
<223> OTHER INFORMATION: sod2-F1; primer

<400> SEQUENCE: 5

```
ggagaagctg acggctgc                                      18
```

<210> SEQ ID NO 6
<211> LENGTH: 48
<212> TYPE: DNA
<213> ORGANISM: Artificial
<220> FEATURE:
<223> OTHER INFORMATION: P3F4-sod2-R3; primer

<400> SEQUENCE: 6

```
cgctgtagtc gaagacgatg tttacgcctt attgaaacca agccaacc     48
```

<210> SEQ ID NO 7
<211> LENGTH: 26
<212> TYPE: DNA
<213> ORGANISM: Artificial
<220> FEATURE:
<223> OTHER INFORMATION: PEN3 F4; primer

<400> SEQUENCE: 7

```
cgctgtagtc gaagacgatg tttacg                             26
```

<210> SEQ ID NO 8
<211> LENGTH: 16
<212> TYPE: DNA
<213> ORGANISM: Artificial
<220> FEATURE:
<223> OTHER INFORMATION: 3T-2D6-Int6-R1; probe

<400> SEQUENCE: 8

```
ctgtaccctt cctccc                                        16
```

<210> SEQ ID NO 9
<211> LENGTH: 25
<212> TYPE: DNA
<213> ORGANISM: Artificial
<220> FEATURE:
<223> OTHER INFORMATION: 5T-sod2-F1-25; probe

<400> SEQUENCE: 9

```
catctgttgg tgtccaaggc tcagg                              25
```

<210> SEQ ID NO 10
<211> LENGTH: 19
<212> TYPE: DNA

```
<213> ORGANISM: Artificial
<220> FEATURE:
<223> OTHER INFORMATION: 2D6-Int6r-F1; primer

<400> SEQUENCE: 10
tgagcccatc tgggaaaca                                            19

<210> SEQ ID NO 11
<211> LENGTH: 22
<212> TYPE: DNA
<213> ORGANISM: Artificial
<220> FEATURE:
<223> OTHER INFORMATION: sod2-R1; primer

<400> SEQUENCE: 11
ccttattgaa accaagccaa cc                                        22

<210> SEQ ID NO 12
<211> LENGTH: 41
<212> TYPE: DNA
<213> ORGANISM: Artificial
<220> FEATURE:
<223> OTHER INFORMATION: PEN3 F4+CTACG; primer

<400> SEQUENCE: 12
ctacgctacg ctacgcgctg tagtcgaaga cgatgtttac g                   41

<210> SEQ ID NO 13
<211> LENGTH: 41
<212> TYPE: DNA
<213> ORGANISM: Artificial
<220> FEATURE:
<223> OTHER INFORMATION: 2D6-P3F4-Int6r-F2; primer
<220> FEATURE:
<221> NAME/KEY: misc_feature
<222> LOCATION: (37)..(37)
<223> OTHER INFORMATION: c, g or t

<400> SEQUENCE: 13
gtagtcgaag acgatgttta cgtgagccca tctgggbaac a                   41

<210> SEQ ID NO 14
<211> LENGTH: 44
<212> TYPE: DNA
<213> ORGANISM: Artificial
<220> FEATURE:
<223> OTHER INFORMATION: P3F4-sod2-R4; primer
<220> FEATURE:
<221> NAME/KEY: misc_feature
<222> LOCATION: (40)..(40)
<223> OTHER INFORMATION: a, g or t

<400> SEQUENCE: 14
gtagtcgaag acgatgttta cgccttattg aaaccaagcd aacc                44

<210> SEQ ID NO 15
<211> LENGTH: 14
<212> TYPE: DNA
<213> ORGANISM: Artificial
<220> FEATURE:
<223> OTHER INFORMATION: 3T-2D6-Int6-R2; probe

<400> SEQUENCE: 15
gtacccttcc tccc                                                 14

<210> SEQ ID NO 16
<211> LENGTH: 16
```

```
<212> TYPE: DNA
<213> ORGANISM: Artificial
<220> FEATURE:
<223> OTHER INFORMATION: 5T-ALK5'-F2; probe

<400> SEQUENCE: 16
ctcattcgtg gagtct                                               16

<210> SEQ ID NO 17
<211> LENGTH: 15
<212> TYPE: DNA
<213> ORGANISM: Artificial
<220> FEATURE:
<223> OTHER INFORMATION: 3T-ALK3'-F2; probe

<400> SEQUENCE: 17
ggaaggaata ttcac                                                15

<210> SEQ ID NO 18
<211> LENGTH: 24
<212> TYPE: DNA
<213> ORGANISM: Artificial
<220> FEATURE:
<223> OTHER INFORMATION: ALK5'-F2; primer

<400> SEQUENCE: 18
tctccatgtg agctccgaat gtcc                                      24

<210> SEQ ID NO 19
<211> LENGTH: 54
<212> TYPE: DNA
<213> ORGANISM: Artificial
<220> FEATURE:
<223> OTHER INFORMATION: P3R2-ALK5'-R5; primer

<400> SEQUENCE: 19
cgatcctgtt tcttagctta gtcaagatcc ccttgctcct tcccggtttt gttc     54

<210> SEQ ID NO 20
<211> LENGTH: 20
<212> TYPE: DNA
<213> ORGANISM: Artificial
<220> FEATURE:
<223> OTHER INFORMATION: ALK3'-F3; primer

<400> SEQUENCE: 20
ggatgccccc agaggccttc                                           20

<210> SEQ ID NO 21
<211> LENGTH: 55
<212> TYPE: DNA
<213> ORGANISM: Artificial
<220> FEATURE:
<223> OTHER INFORMATION: P3R2-ALK3'-R3; primer

<400> SEQUENCE: 21
cgatcctgtt tcttagctta gtcaagatcc tagcagcact ccaaaggacc atgtg    55

<210> SEQ ID NO 22
<211> LENGTH: 30
<212> TYPE: DNA
<213> ORGANISM: Artificial
<220> FEATURE:
<223> OTHER INFORMATION: PEN3 R2 ; primer

<400> SEQUENCE: 22
```
cgatcctgtt tcttagctta gtcaagatcc                                    30

<210> SEQ ID NO 23
<211> LENGTH: 3926
<212> TYPE: DNA
<213> ORGANISM: Homo sapiens

<400> SEQUENCE: 23
ggcggcgcgg cgcggcgctc gcggctgctg cctgggaggg aggccgggca ggcggctgag    60
cggcgcggct ctcaacgtga cggggaagtg gttcggcgg ccgcggctta ctaccccagg   120
gcgaacggac ggacgacgga ggcgggagcc ggtagccgag ccgggcgacc tagagaacga   180
gcgggtcagg ctcagcgtcg gccactctgt cggtccgctg aatgaagtgc ccgcccctct   240
gagcccggag cccggcgctt tccccgcaag atggacggtt tcgccggcag tctcgatgat   300
agtatttctg ctgcaagtac ttctgatgtt caagatcgcc tgtcagctct tgagtcacga   360
gttcagcaac aagaagatga atcactgtg ctaaaggcgg cttttggctga tgttttgagg   420
cgtcttgcaa tctctgaaga tcatgtggcc tcagtgaaaa aatcagtctc aagtaaaggc   480
caaccaagcc ctcgagcagt tattcccatg tcctgtataa ccaatggaag tggtgcaaac   540
agaaaaccaa gtcataccag tgctgtctca attgcaggaa aagaaactct ttcatctgct   600
gctaaaagtg gtacagaaaa aaagaaagaa aaccacaag acagagaga aaaaaagag   660
gaatctcatt ctaatgatca aagtccacaa attcgagcat caccttctcc ccagccctct   720
tcacaacctc tccaaataca cagacaaact ccagaaagca gaatgctac tcccaccaaa   780
agcataaaac gaccatcacc agctgaaaag tcacataatt cttgggaaaa ttcagatgat   840
agccgtaata aattgtcgaa ataccttca cacccaaat taataccaaa agttaccaaa   900
actgcagaca agcataaaga tgtcatcatc aaccaagaag gagaatatat taaaatgttt   960
atgcgcggtc ggccaattac catgttcatt ccttccgatg ttgacaacta tgatgacatc  1020
agaacggaac tgcctcctga aagctcaaa ctggagtggg catatggtta tcgaggaaag  1080
gactgtagag ctaatgttta ccttcttccg accggggaaa tagtttattt cattgcatca  1140
gtagtagtac tatttaatta tgaggagaga actcagcgac actacctggg ccatacagac  1200
tgtgtgaaat gccttgctat acatcctgac aaaattagga ttgcaactgg acagatagct  1260
ggcgtggata aagatggaag gcctctacaa ccccacgtca gagtgtggga ttctgttact  1320
ctatccacac tgcagattat tggacttggc acttttgagc gtggagtagg atgcctggat  1380
ttttcaaaag cagattcagg tgttcattta tgtgttattg atgactccaa tgagcatatg  1440
cttactgtat gggactggca agaaaagca aaggagcag aaataaagac aacaaatgaa  1500
gttgttttgg ctgtggagtt tcacccaaca gatgcaaata ccataattac atgcggtaaa  1560
tctcatattt tcttctggac ctggagcggc aattcactaa caagaaaaca gggaattttt  1620
gggaaatatg aaaagccaaa atttgtgcag tgtttagcat tcttggggaa tggagatgtt  1680
cttactggag actcaggtgg agtcatgctt atatggagca aaactactgt agagcccaca  1740
cctgggaaag gacctaaagt gtaccgccgg aagcaccagg agctgcaagc catgcagatg  1800
gagctgcaga gccctgagta caagctgagc aagctccgca cctcgaccat catgaccgac  1860
tacaaccccca actactgctt tgctggcaag acctcctcca tcagtgacct gaaggaggtg  1920
ccgcggaaaa acatcaccct cattcggggt ctgggccatg agcctttgg ggaggtgtat  1980
gaaggccagg tgtccggaat gcccaacgac ccaagccccc tgcaagtggc ctgtgaagacg  2040
ctgcctgaag tgtgctctga acaggacgaa ctggattcc tcatggaagc cctgatcatc  2100

```
agcaaattca accaccagaa cattgttcgc tgcattgggg tgagcctgca atccctgccc    2160
cggttcatcc tgctggagct catggcgggg ggagacctca agtccttcct ccagagacc    2220 cgccctcgcc cgagccagcc ctcctccctg gccatgctgg accttctgca cgtggctcgg    2280
gacattgcct gtggctgtca gtatttggag gaaaaccact tcatccaccg agacattgct    2340
gccagaaact gcctcttgac ctgtccaggc cctggaagag tggccaagat tggagacttc    2400
gggatggccc gagacatcta cagggcgagc tactatagaa agggaggctg tgccatgctg    2460
ccagttaagt ggatgccccc agaggccttc atggaaggaa tattcacttc taaaacagac    2520
acatggtcct ttggagtgct gctatgggaa atcttttctc ttggatatat gccatacccc    2580
agcaaaagca accaggaagt tctggagttt gtcaccagtg gaggccggat ggacccaccc    2640
aagaactgcc ctgggcctgt ataccggata atgactcagt gctggcaaca tcagcctgaa    2700
gacaggccca actttgccat cattttggag aggattgaat actgcaccca ggacccggat    2760
gtaatcaaca ccgctttgcc gatagaatat ggtccacttg tggaagagga gagaaagtg    2820 cctgtgaggc ccaaggaccc tgaggggtt cctcctctcc tggtctctca acaggcaaaa    2880
cgggaggagg agcgcagccc agctgcccca ccacctctgc ctaccacctc ctctggcaag    2940
gctgcaaaga aacccacagc tgcagaggtc tctgttcgag tccctagagg gccggccgtg    3000 gaaggggac acgtgaatat ggcattctct cagtccaacc ctccttcgga gttgcacagg    3060
gtccacggat ccagaaacaa gcccaccagc ttgtggaacc caacgtacgg ctcctggttt    3120
acagagaaac ccaccaaaaa gaataatcct atagcaaaga aggagccaca cgagaggggt    3180
aacctggggc tggagggaag ctgtactgtc ccacctaacg ttgcaactgg gagacttccg    3240
ggggcctcac tgctcctaga gccctcttcg ctgactgcca atatgaagga ggtacctctg    3300
ttcaggctac gtcacttccc ttgtgggaat gtcaattacg gctaccagca acagggcttg    3360
cccttagaag ccgctactgc ccctggagct ggtcattacg aggataccat tctgaaaagc    3420
aagaatagca tgaaccagcc tgggccctga gctcggtcac acactcactt ctcttccttg    3480
ggatccctaa gaccgtggag gagagagagg caatcaatgg ctccttcaca aaccagagac    3540
caaatgtcac gttttgtttt gtgccaacct attttgaagt accaccaaaa aagctgtatt    3600
ttgaaaatgc tttagaaagg ttttgagcat gggttcatcc tattctttcg aaagaagaaa    3660
atatcataaa aatgagtgat aaatacaagg cccagatgtg gttgcataag gttttatgc    3720 atgtttgttg tatacttcct tatgcttctt ttaaattgtg tgtgctctgc ttcaatgtag    3780
tcagaattag ctgcttctat gtttcatagt tggggtcata gatgtttcct tgccttgttg    3840
atgtggacat gagccatttg aggggagagg gaacggaaat aaaggagtta tttgtaatga    3900
aaaaaaaaaa aaaaaaaaaa aaaaaa                                        3926
```

<210> SEQ ID NO 24
<211> LENGTH: 342
<212> TYPE: DNA
<213> ORGANISM: Artificial
<220> FEATURE:
<223> OTHER INFORMATION: 5'-end sequence of alk

<400> SEQUENCE: 24

```
tcaggaccct aaaggatgcc cggttccagg accaccaaga ccatgctcta ttgctcagta      60
ccactgatgt cccgcttct gaaagtgcta cagtgaccag tgctacgttt cctgcaccga     120
tcaagagctc tccatgtgag ctccgaatgt cctggctcat tcgtggagtc ttgaggggaa     180
```

```
acgtgtcctt ggtgctagtg gagaacaaaa ccgggaagga gcaaggcagg atggtctggc      240
atgtcgccgc ctatgaaggc ttgagcctgt ggcagtggat ggtgttgcct ctcctcgatg      300
tgtctgacag gttctggctg cagatggtcg catggtgggg ac                         342

<210> SEQ ID NO 25
<211> LENGTH: 342
<212> TYPE: DNA
<213> ORGANISM: Artificial
<220> FEATURE:
<223> OTHER INFORMATION: 3'-end sequence of alk

<400> SEQUENCE: 25
ccaccgagac attgctgcca gaaactgcct cttgacctgt ccaggccctg gaagagtggc       60
caagattgga gacttcggga tggcccgaga catctacagg gcgagctact atagaaaggg      120
aggctgtgcc atgctgccag ttaagtggat gcccccagag gccttcatgg aaggaatatt      180
cacttctaaa acagacacat ggtcctttgg agtgctgcta tgggaaatct tttctcttgg      240
atatatgcca taccccagca aaagcaacca ggaagttctg gagtttgtca ccagtggagg      300
ccggatggac ccacccaaga actgccctgg gcctgtatac cg                         342
```

METHOD OF DETERMINING THE ABUNDANCE OF A TARGET NUCLEOTIDE SEQUENCE OF A GENE OF INTEREST

BACKGROUND

A computer readable text file, entitled "SequenceListing.txt," created on or about Jan. 28, 2013 with a file size of about 11.1 kb contains the sequence listing for this application and is hereby incorporated by reference in its entirety.

TECHNICAL FIELD

The present invention relates to a method of measuring gene abundance.

RELATED ART

Some genes are present in multiple copies within one genome. Since the abundance of such genes in a genome may be utilized in genetic diagnosis and affect drug efficacy, there are cases in which it is necessary to understand or measure the abundance of such genes in nucleic acids of a sample of interest (such as a genome). Examples of such detection include measurement of the copy number of a gene, measurement of changes in the amount of a gene, and diagnosis of copy number variation (CNV).

As methods of measuring the abundance of a gene, there are, for example, methods utilizing fluorescence labeling, such as the FISH method (see, for example, Proc. Natl. Acad. Sci. USA, Vol. 89, pp. 5321-5325, June 1992) and the CGH method utilizing competitive DNA binding (see, for example, Japanese National Phase Publication No. 7-505053). In these methods, the abundance of a gene can be verified by allowing a fluorescently-labeled compound to directly react with a chromosome and then performing image processing or observation under a fluorescence microscope. However, in cases where the same gene is present at multiple positions that are relatively close to each other on a chromosome, there are problems in that the gene cannot be identified correctly and use and handling of many reagents is complicated.

From such a standpoint, technologies for efficiently and accurately measuring the abundance of a gene by using a PCR (polymerase chain reaction) technique have been developed, such as real-time PCR (see, for example, Clinical Chemistry pp. 1546-1554 (2009) and WO 2011/043220) and digital PCR (see, for example, Japanese Patent Application Laid-Open (JP-A) No. 2010-538614).

In particular, the technology disclosed in JP-A No. 2010-538614 is a method of determining the relative copy number of a target polynucleotide sequence in a subject genome in which a target gene sequence and a reference gene sequence in a sample containing the subject DNA are amplified and the resulting amplified gene sequences are each assayed by digital PCR, thereby determining the variation in their copy number based on the ratio between the number of amplified polynucleotide molecules containing the target gene sequence and the number of amplified polynucleotide molecules containing the reference gene sequence.

Meanwhile, as a method of amplifying a part of a target nucleic acid of interest when multiple different genes are present in one sample, Japanese National Phase Publication No. 2011-516069 discloses a method which includes a two-step nucleic acid amplification process and a process of rescuing a nucleic acid amplicon of interest between the two steps. In this method, pertinent nucleic acids are amplified using target-specific primers in the first amplification process to produce at least one nucleic acid amplicon containing at least one common primer binding site and the thus obtained nucleic acid amplicon(s) is/are then isolated (rescued) from the target-specific primers before being amplified using a common primer.

Furthermore, in the PCR technique, generally speaking, the respective strands of a double-stranded nucleic acid are amplified using a pair of primers in different directions to produce an amplification product (which may be referred to as an "amplicon") of the subject gene sequence. It is known, therefore, that in the process of nucleic acid amplification performed by such a pair of primers, a double-stranded amplicon initially accumulates in a reaction system in an exponential fashion and then, as the amounts of the thus produced and accumulated complementary amplicon strands increase, the rate of the amplification reaction is decreased and the amplification reaction eventually ends (plateau phase). Once the system reaches this plateau phase, since nucleic acid amplification no longer takes place, the amount of amplicon does not increase. In order to effect a continuous increase in the accumulated amount of amplicon without reaching this kind of a plateau phase, "Linear-After-The-Exponential PCR (LATE-PCR)" is known, in which a pair of primers is used in amounts having a given difference therebetween (see, for example, Japanese National Phase Publication No. 2005-512577).

In addition, when detecting a fusion gene, multiplex PCR in which specific primers are designated for each variant (see, for example, JP-A No. 2012-100628) is often employed. In multiplex PCR, it is necessary to prepare a number of primers and to perform optimization taking into consideration the possibility that each of the primers might produce a dimer. It is necessary to re-prepare primers via this optimization process and examine whether or not the gene is measurable via experimentation. Moreover, as the number of primers increases, this optimization process becomes more difficult, requiring a very long time, a tremendous amount of labor and high costs in order to determine the optimum primer set.

SUMMARY OF THE INVENTION

Problems to be Solved by the Invention

However, even in cases in which nucleic acid amplification is performed with a target gene sequence and a reference gene sequence and their copy number is determined based on the ratio of the amounts of the respective amplification products, different primers are employed in order to amplify each of the target and reference gene sequences. In such cases in which different primers are employed, their amplification efficiencies are often different. Furthermore, in cases where nucleic acid amplification is performed using the PCR technique, as a result of the plateau phase described above, at a high number of PCR cycles, the amounts of amplification products become constant regardless of the intrinsic abundances of the respective nucleic acids. Therefore, when an attempt is made to measure the abundance of a gene in a genome using the PCR technique, the results may not accurately reflect the intrinsic abundance of the gene. In addition, in cases where multiplex PCR is employed, since a large number of primers must be prepared, there are problems related, for example, to costs, labor and/or time required for the optimization process.

Therefore, an object of the present invention is to provide a method of measuring gene abundance according to which the abundance(s) of a gene(s) in a nucleic acid contained in a subject sample is/are measured more accurately and simply as compared to conventional techniques.

Means for Solving the Problems

The present invention is as follows.

[1] A method of measuring gene abundance, which includes: obtaining at least two types of amplification product, each of which contains a single additional base sequence and corresponds to each of at least two genes, by amplifying, in one reaction solution, nucleic acids encoding the at least two genes whose abundances in nucleic acids contained in a subject sample may be different, using a first primer set, which includes at least two types of first primer, each of which is capable of introducing the single additional base sequence to a resulting amplification product and corresponds to each of the at least two genes, and a second primer for amplifying a nucleic acid containing the single additional base sequence; and determining the abundances of the at least two genes based on detected signals corresponding to the abundances of the at least two types of amplification product.

[2] The method according to [1], in which the first primers contain the single additional base sequence and a base sequence capable of hybridizing to the base sequence of a region to be amplified of the respective nucleic acids encoding each of the at least two genes.

[3] The method according to [1] or [2], in which the second primer contains a base sequence capable of hybridizing to the single additional base sequence or to the base sequence complementary to the single additional base sequence.

[4] The method according to any one of [1] to [3], in which the single additional base sequence includes a base sequence that is non-homologous to the base sequence in a respective region to be amplified of the respective nucleic acids encoding each of the at least two genes.

[5] The method according to any one of [1] to [4], in which the first primer set includes the first primers and third primers, the third primers being used for amplifying a base sequence in the strand complementary to the respective base sequences to which the first primers hybridize, and the third primers do not contain the single additional base sequence.

[6] The method according to [5], in which, in the reaction solution, the abundance of the third primers is, by molar ratio, 0.25 to 4 times the abundance of the first primers.

[7] The method according to any one of [1] to [6], in which, in the reaction solution, the abundance of the second primer is, by molar ratio, 1 to 400 times the abundance of each of the primers contained in the first primer set.

[8] The method according to any one of [1] to [7], in which the reaction solution further contains at least two types of detection probe that respectively recognize each of the at least two types of amplification product.

[9] The method according to any one of [1] to [8], in which the first primers contain at least one selected from the group consisting of bases that are mismatched, or bases that are degenerate, with respect to the base sequence of a region to be amplified.

[10] The method according to any one of [1] to [9], in which the second primer has a higher Tm value than the first primers.

[11] The method according to any one of [1] to [10], in which the second primer further contains an additional sequence that is different from the single additional base sequence and from the base sequence that is complementary to the single additional base sequence.

[12] The method according to any one of [1] to [11], in which at least one of the at least two genes is a reference gene whose abundance in the nucleic acids contained in the subject sample is known in advance and at least one other gene of the at least two genes is a target gene whose abundance in the nucleic acids contained in the subject sample is to be measured.

[13] The method according to [12], which includes determining the abundance of the target gene in the nucleic acids contained in the subject sample by comparing the detection signal of an amplification product derived from the reference gene with a detection signal of an amplification product derived from the target gene.

[14] The method according to any one of [1] to [11], in which at least one of the at least two genes is a gene region located on the 5'-side upstream of a fusion point of a fusion gene and at least one other gene of the at least two genes is a gene region located on the 3'-side downstream of the fusion point of the fusion gene.

[15] The method according to [14], which further includes detecting the presence of the fusion gene in the sample by comparing the detection signal of an amplification product derived from the gene region on the 5'-side and the detection signal of an amplification product derived from the gene region on the 3'-side.

[16] The method according to any one of [1] to [15], in which the abundances of the at least two genes are determined by Tm analysis of at least two detection signals corresponding to the respective genes.

[17] The method according to any one of [1] to [16], in which the signals that are used to determine the abundances of the at least two genes are obtained in terms of absorbance or fluorescence values measured at the same wavelength.

[18] The method according to [16] or [17], in which the abundances in the nucleic acids contained in the subject sample are determined by areal analysis of results from Tm analysis.

[19] A gene measurement kit for use in the method according to any one of [1] to [4] and [7] to [18], which contains a first primer set that includes at least two types of first primer, each of which is capable of introducing a single additional base sequence to a resulting amplification product and corresponds to each of the at least two genes; and a second primer for amplifying a nucleic acid containing the single additional base sequence.

[20] A gene measurement kit for use in the method according to any one of [5] to [18], which contains a first primer set that includes at least two types of first primer, each of which is capable of introducing a single additional base sequence to a resulting amplification product and corresponds to each of the at least two genes; a second primer for amplifying a nucleic acid containing the single additional base sequence; and third primers that are used for amplifying a base sequence in the strand complementary to the respective base sequences to which the first primers hybridize, and that do not contain the single additional base sequence.

[21] The gene measurement kit according to [19] or [20], which further includes at least two detection probes, each of which has a base sequence capable of hybridizing to the region to be amplified of the at least two genes and contains a label.

[22] The gene measurement kit according to [21], wherein the label is a fluorescent label.

[23] A gene measuring apparatus to which the method according to any one of [1] to [18] can be applied, the apparatus including a detection unit that detects at least two signals corresponding to the abundances of the amplification products, each of which contains the single additional base sequence introduced by the first primers and corresponds to the at least two genes amplified by the second primer; and an arithmetic unit that calculates the abundances of the at least two genes by comparing the at least two signals detected by the detection unit.

[24] A gene measuring system for carrying out the method according to any one of [1] to [18], the system including a detection device that detects at least two signals corresponding to the abundances of the amplification products, each of which contains the single additional base sequence introduced by the first primers and corresponds to the at least two genes amplified by the second primer; and an arithmetic device that calculates the abundances of the at least two genes by comparing the at least two signals detected by the detection device.

[25] A method of genetic diagnosis performed using the method according to any one of [1] to [18].

Effects of the Invention

According to the present invention, a method of measuring gene abundance is provided, according to which the abundance(s) of a gene(s) in nucleic acids contained in a subject sample is/are measured more accurately and simply as compared to conventional techniques.

DETAILED DESCRIPTION OF THE INVENTION

Mode for Carrying Out the Invention

Figure 1A:
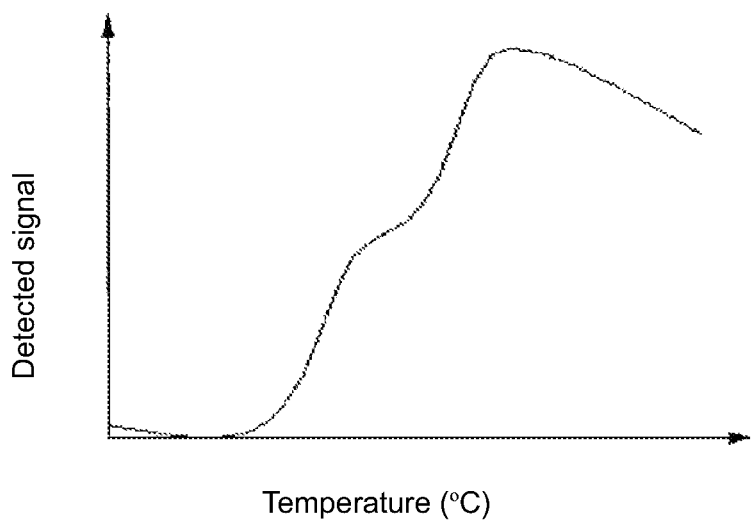
FIG. 1(A) shows one example of a melting curve of a nucleic acid mixture and FIG. 1(B) shows one example of a differential melting curve.

The method of measuring gene abundance according to the present invention includes the steps of: obtaining at least two types of amplification product, each of which contains a single additional base sequence and corresponds to each of at least two genes, by amplifying, in one reaction solution, nucleic acids encoding the at least two genes, whose abundances in a subject sample may be different using a first primer set, which includes at least two types of first primer, each of which is capable of introducing the single additional base sequence to a resulting amplification product and corresponds to each of the at least two genes, and a second primer for amplifying a nucleic acid containing the single additional base sequence; and determining the abundances of the at least two genes based on detected signals corresponding to the abundances of the at least two types of amplification product.

It is noted here that the term "gene" as used herein also encompasses the concept of a "gene region", which indicates a region of a gene. Further, a "gene" may be any gene as long as it is encoded by a base sequence, and the term "gene" encompasses not only genes that express a specific function, but also genes that do not express any specific function.

In the measurement method according to the present invention, since the amplification of the respective nucleic acids of the above-described at least two genes (hereinafter, referred to as "genes of interest") is performed by allowing the first primer set containing prescribed first primers and the second primer to exist in one reaction, as a result of the nucleic acid amplification performed by the prescribed first primers, a single additional base sequence is introduced to the resulting multiple types of amplification product, each of which corresponds to the respective genes of interest. Accordingly, even when multiple genes of interest exist in one reaction solution, a single, that is, common, additional base sequence is introduced to the corresponding amplification products. The multiple types of nucleic acid (or amplification product) to which this single additional base sequence is introduced and that correspond to the respective genes of interest all contain a single common additional base sequence; therefore, they can be uniformly amplified with one second primer. As a result, even when the abundances of the multiple genes in the reaction solution are different, the abundances of the amplification products derived from the respective genes obtained as a result of nucleic acid amplification by the same second primer reflect the abundances of the respective genes, which is different from the case in which nucleic acid amplification is performed with different primers. Consequently, the abundances of at least two genes in nucleic acids contained in a subject sample can be measured more accurately and simply than by conventional techniques.

In the present invention, matters concerning the respective sequences of the nucleic acids, detection probes and primers in a sample of interest that are described on the basis of the complementary relationships among those sequences are, unless otherwise specified, also applicable to their complementary sequences. Further, when the description of a particular base sequence is applied to a complementary base sequence thereof, the description of base sequences recognized by the particular base sequence in the present invention should be applied, provided that recognition by the particular base sequence is replaced with recognition by a complementary base sequence of the particular base sequence, within the range of the common general technical knowledge of those skilled in the art.

In the present invention, the term "Tm value" is a temperature at which a double-stranded nucleic acid dissociates (dissociation temperature: Tm) and is generally defined as the temperature at which the absorbance at 260 nm reaches 50% of the total increase in the absorbance. That is, when a solution containing a double-stranded nucleic acid such as a double-stranded DNA is heated, the absorbance of the solution at 260 nm increases. This is because the hydrogen bonds between the strands of the double-stranded DNA are broken by the heat to cause dissociation of the double-stranded DNA into single-stranded DNAs (DNA melting). When the double-stranded DNA is completely dissociated into single-stranded DNAs, the solution exhibits an absorbance of about 1.5 times the absorbance at the start of the heating (the absorbance of the solution containing only the double-stranded DNA), and melting may be deemed complete due to this change in the absorbance. The Tm value is defined based on this phenomenon. In the present invention, unless otherwise specified, the term "Tm value" means a temperature at which 50% of the bases form a double strand with the remaining 50% being dissociated into single strands.

In the present invention, the term "template nucleic acid" or "template" means a base sequence to which a primer anneals as a template at the time of nucleic acid amplification.

In the present invention, the term "process" or "step" encompasses not only a discrete process/step, but also a process/step that cannot be clearly distinguished from other processes/steps as long as the intended object of the process/step is achieved.

Further, in the present invention, those numerical ranges that are described using the term "to" denote a range which includes the numerical values stated before and after "to" as the minimum and maximum values, respectively.

Moreover, in the present specification, when reference is made to the amount of a component in a composition, in cases where the composition contains multiple substances corresponding to the component, the indicated amount means the total amount of the multiple substances present in the composition unless otherwise specified.

The outline of the present invention will now be explained.

<Method of Measuring Gene Abundance>

The method of measuring gene abundance according to the present invention includes the steps of: obtaining at least two types of amplification product, each of which contains a single additional base sequence and corresponds to each of at least two genes, by amplifying, in one reaction solution, nucleic acids encoding the at least two genes, whose abundances in a subject sample may be different, using a first primer set, which includes at least two types of first primer, each of which is capable of introducing the single additional base sequence to a resulting amplification product and corresponds to each of the at least two genes, and a second primer for amplifying a nucleic acid containing the single additional base sequence (hereinafter, referred to as "the nucleic acid amplification step"); and determining the abundances of the at least two genes based on detected signals corresponding to the abundances of the at least two types of amplification product (hereinafter, referred to as "the abundance measurement step").

The nucleic acid amplification step includes obtaining at least two types of amplification product, each of which contains a single additional base sequence and corresponds to each of at least two genes, by amplifying, in one reaction solution, nucleic acids encoding the at least two genes, whose abundances in a subject sample may be different, using a first primer set, which includes at least two types of first primer, each of which is capable of introducing the single additional base sequence to a resulting amplification product and corresponds to each of the at least two genes, and a second primer for amplifying a nucleic acid containing the single additional base sequence.

The above-described reaction solution contains at least two types of gene, that is, at least two types of gene of interest.

The genes of interest may respectively have a different abundance within nucleic acids contained in a subject sample and generally include genes having different abundances in the nucleic acids contained in the subject sample; however, the genes of interest may include genes having the same abundance. The base sequences that encode the genes of interest in the reaction solution correspond to the nucleic acids which serve as templates in the nucleic acid amplification described below.

The sample which may serve as the source of the nucleic acids in the reaction solution is not particularly restricted. Examples of the sample include those that are derived from or may be derived from a given biological source, such as blood, oral mucosa suspensions, somatic cells of nail, hair and the like, germ cells, milk, ascitic fluid, paraffin-embedded tissues, gastric juices, gastric lavage fluid, peritoneal fluid, amniotic fluid and cell cultures. The nucleic acid serving as a template may be used directly from the source or after being pre-treated to modify the properties of the sample.

For example, in cases where whole blood is used as the sample, genomic DNA can be isolated therefrom to prepare the nucleic acids of the genes of interest. The isolation of genomic DNA from whole blood can be performed by a conventional method known in the art. For example, a commercially available genomic DNA isolation kit (trade name: GFX GENOMIC BLOOD DNA PURIFICATION KIT; manufactured by GE Healthcare Biosciences Inc.) may be employed.

The nucleic acids contained in the reaction solution may be single-stranded or double-stranded. The nucleic acid sequences contained in the reaction solution may be, for example, DNA or RNA such as total RNA or mRNA. Further, in the present invention, since the nucleic acid amplification is performed by allowing the below-described multiple types of primers to exist in the reaction solution, the reaction solution after the nucleic acid amplification step also contains amplification products produced by the nucleic acid amplification. Accordingly, in the present invention, these amplification products are also included as the nucleic acids contained in the reaction solution.

The genes of interest in the reaction solution may be the subjects for which the abundance is measured in the present invention, as long as they are at least two types of gene. Preferably, at least one of the genes of interest is a reference gene whose abundance in the nucleic acids contained in a subject sample is known in advance and at least one other gene is a target gene whose abundance in the nucleic acids contained in the subject sample is to be measured. In this manner, by utilizing at least one of the genes of interest as a reference gene whose abundance in the nucleic acids contained in a subject sample is known, the abundance of the target gene in the nucleic acids contained in the subject sample can be easily determined using the abundance of the reference gene as a reference (index).

Here, the term "abundance in the nucleic acids contained in a subject sample" means, for example, the copy number of a gene having a prescribed size, the size of one copy of a gene as a whole in a nucleic acid(s) contained in a sample, or the amount/size of increase or decrease in a gene associated with a disease, a specific region of a gene which corresponds to a functional domain when translated into a protein, a tandem repeat or a microsatellite. In the measurement method according to the present invention, for example, from the standpoints of the sensitivity and simplicity thereof, it is preferred that the subject of the abundance measurement be the copy number of a gene.

The gene which may be employed as the above-described reference gene is not particularly restricted as long as it is a gene whose abundance is known to be the same among individuals or a gene whose abundance does not change over time and is relatively stable, and examples of such genes include RNaseP, sod2, COL8A1 and gamma-actin genes. Further, the combination of the reference gene and target gene is not particularly restricted. The genes may be on the same chromosome in a genome map or may be remotely positioned on different chromosomes in a genome map. The reference gene and target gene are selected as appropriate and there is no particular restriction on the selection.

The gene which may be employed as the target gene varies depending on the intended use of the measured abundance. Examples of the target gene include genes exhibiting polymorphism; genes whose abundance is increased or decreased due to a disease; genes in which a base(s) is/are deleted from the base sequence due to a disease; and genes whose expression level varies depending on the sample.

Further, the combination of the reference gene and the target gene can be selected as appropriate based on the nature of the target gene. For example, in the case of detecting a copy number polymorphism among individuals, a gene whose abundance is known to be the same among the individuals is selected as the reference gene and the target gene may be, for example, a gene exhibiting polymorphism. In the case of detecting the abundance of a gene which serves as a target for a therapeutic agent of a disease, a gene whose abundance does not change over time and is relatively stable is selected as the reference gene and the target gene may be, for example, a gene whose abundance is increased or decreased due to the disease or a gene in which a base(s) is/are deleted due to the disease. Further, in the case of detecting the expression level of an RNA, for example, a housekeeping gene is selected as the reference gene and the target gene may be, for example, a gene whose expression level varies depending on the sample.

Further, in another embodiment, it is also preferred that at least one of the genes of interest is present in a gene region located on the 5'-side upstream of a fusion point of a fusion gene (hereinafter, also referred to as the "5'-gene region") and at least one other gene is present in a gene region located on the 3'-side downstream of the fusion point of the fusion gene (hereinafter, also referred to as the "3'-gene region"). In this manner, by comparing the abundance of a 5'-gene region and that of a 3'-gene region, for example, the presence or absence of a mutation in a fusion gene can be easily detected.

The fusion gene may be any gene as long as it is formed by fusion between a part of a gene and a part of another gene and exists as one single gene. The fusion gene is not particularly restricted and specific examples thereof include an ALK fusion gene, a BCR-ABL fusion gene, an AML1-MTG8 fusion gene, a RET fusion gene and a ROS1 fusion gene.

This embodiment will now be described in detail taking an ALK fusion gene as an example.

The ALK gene (NCBI Accession No. NM 004304.4) encodes ALK (anaplastic lymphoma kinase) receptor tyrosine kinase.

As ALK fusion genes, for example, the EML4-ALK fusion gene described in J. Clin. Oncol. 2009, Sep. 10; 27(26): 4232-5 and fusion genes that are formed with various genes such as KIF5B, KLC1 and TFG are known.

In the measurement method according to the present invention, paying attention only to one of the genes constituting the fusion gene, the abundance of a gene region located on the 5'-side upstream of the fusion point of the fusion gene and the abundance of a gene region located on the 3'-side downstream may be measured and compared.

The term "fusion point" refers to a boundary at which two different genes are fused. For example, in the ALK gene, the 4,125th base (which corresponds to the 1,760th base of SEQ ID NO:23) serves as the fusion point.

Here, the 5'-gene region and the 3'-gene region for which the abundance is measured are not particularly restricted as long as they are located upstream and downstream of the fusion point, respectively. Gene abundance can be measured as long as the 5'-gene region and the 3'-gene region for which the abundance is measured are located at least one base away from the fusion point; however, it is preferred that these gene regions are located sufficiently away from the fusion point. For example, these gene regions are located at a distance of preferably not less than about 10 bases, still more preferably not less than about 50 bases, away from the fusion point.

Further, a fusion point generated in association with a fusion gene mutation may exist at multiple points on a nucleic acid. Therefore, by appropriately setting the distances of the 5'-gene region and the 3'-gene region from the fusion point(s) in accordance with the type of fusion gene mutation to be measured, the type of detectable fusion gene mutation can be modified freely, so that more variants can be rendered detectable.

It is noted here that the distance (the number of bases) between a fusion point and a gene region is calculated by reference to the 5'-end of a primer hybridized closest to the fusion point among those primers hybridizing to a 5'-gene region or 3'-gene region that serves as a gene of interest.

In the present specification, the fusion gene is not restricted to an ALK fusion gene. The method according to the present invention can be applied to any gene in the same manner as in the case of an ALK fusion gene, as long as the gene is one whose base sequence is registered in a database of GenBank or the like.

The first primer set contains first primers and amplifies each strand of the double-stranded nucleic acids of the regions to be amplified in the genes of interest. The first primers are capable of introducing a single additional base sequence to the resulting amplification products and correspond to each of the at least two genes.

Here, the regions to be amplified correspond to a part of the respective base sequences encoding the genes of interest and have a length of preferably 40 to 5,000 bases, more preferably 50 to 1,000 bases, and still more preferably 60 to 200 bases. By controlling the length of the regions to be amplified to this range, there are the advantages that, for example, the reaction time in the nucleic acid amplification step can be shortened; the amplification-inhibiting effect can be alleviated; the progress of multiple nucleic acid amplifications can be ensured; and measurement accuracy can be improved.

Here, the expression "correspond to each of the at least two genes" means that the amplification can be performed by setting the base sequences characteristic of the genes of interest as the regions to be amplified. Therefore, in the nucleic acid amplification step, the number of first primers used is set in accordance with the number of types of genes of interest.

The first primers are required to be capable of introducing a single additional base sequence to the resulting amplification products. Here, the expression "capable of introducing a single additional base sequence to the resulting amplification products" means not only that amplification products containing the single additional base sequence itself, which consists of a prescribed base sequence, are produced, but also that amplification products containing the base sequence complementary to the prescribed base sequence are produced.

In order to ensure that the first primers are capable of introducing a single additional base sequence to the resulting amplification products, the first primers may be made to contain a single additional base sequence and a base sequence which can be amplified using, as a template, a part of the base sequence of the respective nucleic acids encoding the genes of interest. The first primers may also be made to contain a linker sequence between these base sequences. The base sequence which can be amplified using a part of the base sequence of the respective nucleic acids encoding the genes of interest as a template may be, for example, a base sequence capable of hybridizing to the base sequence of the above-described regions to be amplified. From the standpoints of, for example, the operational simplicity and the sensitivity of the measurement method, it is preferred that the first primers be a combination of the single additional base sequence and a base sequence capable of hybridizing to the base sequence of the regions to be amplified of the genes of interest.

Here, the term "single additional base sequence" means one (a single) additional base sequence which can be commonly introduced to all amplification products that may exist in one reaction system used in one measurement, and the term also encompasses sequences that are complementary to the single additional base sequence. The "single additional base sequence" contained in the first primers may be either the above-described single additional base sequence or the base sequence complementary thereto. Hereinafter, unless otherwise specified, the "single additional base sequence" introduced to the amplification products and the "single additional base sequence" contained in the first primers are simply and collectively referred to as a "single additional base sequence".

The structure (base sequence and length) of the single additional base sequence is not particularly restricted and any given sequence may be selected. Since the single additional base sequence is a base sequence to be commonly introduced to all of the resulting amplification products, it is preferably a sequence composed of a base sequence which is non-homologous to the base sequence in the respective regions to be amplified of the at least two genes, more preferably a sequence composed of a base sequence which is non-homologous to the base sequence of a region including the region to be amplified and its adjacent regions (for example, a range of not more than 1,000 bases in length), still more preferably a sequence composed of a base sequence which does not exist in the base sequences of the genes contained in the reaction solution. As a result, there are the advantages that, for example, the accuracy of nucleic acid amplification performed by the below-described second primer can be improved. Here, the term "non-homologous" means that the sequence has a homology of not more than 50%, and preferably not more than 25%, to the region to be amplified.

Here, the term "a base sequence capable of hybridizing to the base sequence of the regions to be amplified" means a sequence which is, under normal nucleic acid amplification conditions, capable of annealing to a single-stranded nucleic acid (template nucleic acid) containing the base sequence to be amplified to form a double-stranded nucleic acid with the template nucleic acid.

In the first primers, the base sequence capable of hybridizing to the base sequence of the regions to be amplified is not particularly restricted as long as it is capable of amplifying the base sequence of the template nucleic acid contained in the regions to be amplified, and those skilled in the art would be able to appropriately design such a base sequence on the basis of the base sequence of the gene of interest.

The "base sequence capable of hybridizing" related to the first primers includes a base sequence which is completely complementary to the base sequence of the template nucleic acid and, under the below-described nucleic acid amplification conditions, the "base sequence capable of hybridizing" may also include a base sequence obtained by deleting, substituting or adding one or more bases in the completely complementary base sequence to such an extent that the affinity to a single-stranded nucleic acid is not significantly impaired. In cases where a base is inserted, deleted or substituted, the position of the insertion, deletion or substitution is not particularly restricted. The number of inserted, deleted or substituted bases is, for example, 1 base or 2 or more bases. The number of inserted, deleted or substituted bases is variable depending on the overall length of the first primers; however, it is, for example, 1 to 10 bases, and preferably 1 to 5 bases.

Further, in order to give preference to the nucleic acid amplification performed by the second primer, the first primers may also contain various additional base sequences that are different from the single additional base sequence, or an additional base sequence having a prescribed length (hereinafter, these are collectively referred to as an "additional base sequence for adjustment"). As the additional base sequence for adjustment, those described in the following may be used individually, or two or more that are appropriately selected may be used in combination.

It is preferred that this kind of additional base sequence for adjustment contains at least one selected from the group consisting of bases that are either mismatched or degenerate with respect to the base sequence of the regions to be amplified. The type and number of mismatched or degenerate bases are not particularly restricted and may be decided in view of adjustment of the expected Tm value, effects on the amplification efficiency and adjustment of the number of identical primer molecules.

Further, as another additional base for adjustment, a degradation-inducing base selected from the group consisting of a uracil base, AP sites and RNA bases may be introduced as well. In cases where this kind of degradation-inducing base is introduced, the Tm values of the first primers for the amplification products can be lowered by degrading the degradation-inducing base after obtaining the amplification products generated by the first primers. As a result, there are the advantages that, for example, nucleic acid amplification by the second primer can proceed preferentially.

The length and the Tm value of the respective first primers are normally 12 mer to 60 mer and 40° C. to 85° C., and preferably 16 mer to 50 mer and 50° C. to 80° C., respectively; however, they are not restricted to these ranges.

Further, in the first primers, the length of the single additional base sequence and the length of the base sequence capable of hybridizing to the base sequence of the regions to be amplified of the genes may be the same or different.

Moreover, in the first primers, the single additional base sequence may be arranged at any position. Preferably, the single additional base sequence is arranged at the 5'-end of the respective first primers. By arranging the single additional base sequence on the 5'-end side of the base sequence that hybridizes to the regions to be amplified of the genes, the reaction in the initial amplification of the genes of interest by the first primers cannot be inhibited, for example.

The second primer is used to amplify a nucleic acid that contains the single additional base sequence amplified by the first primer set. As a result, the resulting amplification products containing the single additional base sequence that are obtained by using the first primer set including the first primers can be further amplified and accumulated in the reaction solution.

The second primer may contain a base sequence capable of hybridizing to the single additional base sequence or to the base sequence complementary to the single additional base sequence. In order to prevent hybridization between the single additional base sequence of the first primers and the second primer, it is preferred that the second primer contain a base sequence capable of hybridizing to the base sequence complementary to the single additional base sequence contained in a part of the first primers, that is, a base sequence homologous to the single additional base sequence contained in a part of the first primers. As a result, the resulting amplification products containing the single additional base sequence can be efficiently and effectively accumulated in the reaction solution.

In the second primer, one or more bases may be further deleted, substituted or added as long as the second primer can form a double-stranded nucleic acid with the single additional base sequence or the base sequence complementary thereto under normal nucleic acid amplification conditions. In cases where a base is inserted, deleted or substituted, the position of the insertion, deletion or substitution is not particularly restricted. The number of inserted, deleted or substituted bases is, for example, 1 base or 2 bases or more. The number of inserted, deleted or substituted bases is variable depending on the total length of the second primer; however, it is, for example, 1 to 10 bases, and preferably 1 to 5 bases.

Preferably, the second primer contains a sequence homologous to the single additional base sequence contained in a part of the first primers. As a result, for example, the measurement accuracy can be improved. Here, in the second primer, the term "homologous" to the single additional base sequence means that the sequence has a homology of not less than 80% to the single additional base sequence. In the second primer, the sequence homologous to the single additional base sequence has a homology of preferably not less than 90%, and most preferably 100%, to the single additional base sequence.

In the second primer, in order to allow the nucleic acid amplification by the second primer to proceed in preference to the nucleic acid amplification by the first primers, it is preferred that the Tm value of the second primer (which means the Tm value for the amplification products) be higher than those of the first primers (which means the Tm value of the respective regions to be amplified of the nucleic acids encoding the at least two genes or the Tm value of the amplification products).

Therefore, the second primer may contain an additional sequence that is different from the single additional base sequence and its complementary base sequence and that is capable of adjusting the second primer to have a higher Tm value than the first primers (hereinafter, referred to as an "additional base sequence for adjustment"). As a result, the Tm value of the second primer for the respective amplification products can be increased. The additional sequence used for this purpose is not particularly restricted, and examples thereof include base sequences having a high GC content.

Further, the second primer may also have an artificial nucleic acid introduced thereto. Examples of this kind of artificial nucleic acid include LNAs, BNAs and PNAs.

In addition, in order to ensure that the second primer has a higher Tm value than the first primers, an RNA primer may also be introduced to the second primer. Moreover, an MGB (Minor Group Binder), which is a Tm enhancer that increases the melting temperature, may also be added.

The length and Tm value of the second primer are usually 12 mer to 60 mer and 40° C. to 85° C., and preferably 16 mer to 50 mer and 50° C. to 80° C., respectively; however, they are not restricted to these values.

Here, in cases where the Tm value of the second primer is set to be higher than those of the first primers, it is preferred that the Tm value of the second primer is higher than those of the first primers by at least 0.1° C., 1° C., 3° C. or 5° C. Further, it is preferred that the difference between the Tm value of the second primer and those of the first primers are less than 30° C., 25° C. or 20° C. Accordingly, the Tm value of the second primer is preferably higher than those of the first primers by 0.1° C. to 30° C., and more preferably by 1° C. to 30° C., 3° C. to 30° C. or 5° C. to 25° C.

Further, in cases where the Tm value of the second primer is set to be higher than those of the first primers, it is preferred that the Tm value of the second primer is 50° C. to 85° C. and those of the first primers is 40° C. to 75° C. It is more preferable that the Tm value of the second primer is 55° C. to 80° C. and those of the first primers is 50° C. to 75° C.

The first primer set includes, in addition to the first primers, other primer(s) for amplifying the other single-stranded nucleic acid of the double-stranded nucleic acid of the respective genes of interest. This other primer may be one which is the same as a first primer and designed in the same manner to include the single additional base sequence (a set consisting of a pair of the first primers) or a third primer which is used to amplify a single-stranded complementary strand to which the first primers hybridize and does not include the single additional base sequence. The third primer may be any primer as long as it does not include the single additional base sequence and does include a base sequence capable of hybridizing to a base sequence of a single-stranded complementary strand of the genes of interest which is recognized by the first primers.

With regard to the term "base sequence capable of hybridizing" relating to the third primer, those matters described above in relation to the first primers can be applied without modification.

Further, the second primer can form a second primer set with another primer used for amplifying the other nucleic acid of the double-stranded nucleic acid having the single additional base sequence. This other primer included in the second primer set may form a set consisting of a pair of the above-described second primers, and the other primer can also form the second primer set with the third primers that are included in the first primer set. That is, in cases where the first primer set includes the third primers, the third primers can form a pair with each of the first primers and the second primer (sets consisting of the first primers or the second primer with the respective third primers), so that both base sequences of the double-stranded nucleic acid of the respective genes of interest can be amplified.

The primer set to be used in the nucleic acid amplification step may be, for example, a combination of a set consisting of a pair of the first primers and a set consisting of a pair of the second primers or a combination of the first, second and third primers. Further, in this case, the first and second primers may also contain the additional base sequence for adjustment.

The combination is not restricted to those described above, and examples thereof include the following:

a combination of first primers that have the base sequence complementary to the single additional base sequence as well as to the base sequence of the regions to be amplified of the genes of interest, a second primer that contains no additional base sequence for adjustment, and third primers;

a combination of first primers having a lower Tm value than the second primer, a second primer having a higher Tm value than the first primers, and third primers;

a combination of first primers having a higher Tm value than the second primer, a second primer having a lower Tm value than the first primers, and third primers;

a combination of first primers having a lower Tm value than the second primer and containing an additional sequence for adjustment, a second primer that contains no mismatched or degenerate base, and third primers;

a combination of first primers having a lower Tm value than the second primer and containing an additional base sequence for adjustment such as a mismatched or degenerate base, a second primer that contains no additional base sequence for adjustment such as a mismatched or degenerate base, and third primers;

a combination of first primers having a lower Tm value than the second primer and containing an additional sequence for adjustment and a mismatched or degenerate base(s), a second primer that contains no additional base sequence for adjustment such as a mismatched or degenerate base, and third primers;

a combination of first primers that do not contain a substitution or the like with respect to the single additional base sequence or the base sequence of the regions to be amplified of the genes of interest, a second primer having a higher Tm value than the first primers and containing an additional base sequence for adjustment, and third primers;

a combination of first primers that contain an additional base sequence such as a mismatched or degenerate base, a second primer having a higher Tm value than the first primers and containing an additional base sequence for adjustment such as a mismatched or degenerate base, and third primers; and a combination of first primers containing a mismatched or degenerate base(s), a second primer having a higher Tm value than the first primers and containing an additional base sequence for adjustment such as a mismatched or degenerate base, and third primers.

In this case, with regard to the configuration of the first primers corresponding to the respective genes of interest contained in the reaction solution, the first primers may be of the same type (for example, neither of the first primers contains a mismatched or degenerate base), or the first primers may be of different types (for example, one of the first primers does not contain a mismatched or degenerate base and the other contains a mismatched or degenerate base(s)); however, in view of, for example, ensuring the nucleic acid amplification of multiple genes of interest with the same amplification efficiency, it is preferred that the first primers are of the same type.

In cases where third primers are employed, the reaction solution may contain the third primers in an amount by molar ratio of 0.25 to 4 times the amount of the first primers forming a pair with the third primers. When the amount is 0.25 times or more, for example, it tends to be the case that amplification can be performed without significantly impairing the amplification balance of the first and third primers, while when the amount is 4 times or less, there are the advantages that, for example, the second primer easily reacts with the amplification products of the third primers.

The amount of the third primers may be equal to that of the first primers. In addition, in order to control the primer sequences and reagent formulations that are actually employed as well as the values of the detection results to be obtained, the third primers may be adjusted and optimized by finely increasing or decreasing the amount thereof. As a result, it may be possible to attain the advantage that the intensity of the detection signal for the reference gene or the target gene or that of the detection signal for the 5'-gene region or the 3'-gene region can be made adjustable, as well as the advantage that the amplification efficiencies of the reference gene and the target gene can be adjusted.

From the standpoint of, for example, enabling an easier transition to the reaction by the second primer, the amount of the third primers may be, by molar ratio, preferably about 1 to 4 times, and more preferably 1 to 2 times, with respect to the amount of the first primers.

Further, in cases where the amount of the third primers is less than that of the first primers, since the amount of the third primers is relatively small in the reaction solution, for example, the first primers and the second primer undergo their respective reactions in such a manner that they compete for the third primers. As a result, there may be the advantage that, for example, a reagent can be prepared that is likely to allow the amplification of the reference and target genes to reach a reaction plateau. In this case, the amount of the third primers may be, by molar ratio, about 0.25 times to 1 time, and more preferably 0.5 times to 1 time, with respect to the amount of the first primers.

Further, the reaction solution may contain the second primer in an amount by molar ratio equal to or larger than the respective primers that are included in the first primer set. This has the advantage that, for example, the amplification products generated by nucleic acid amplification performed by the first primer set can be reliably amplified. In addition, one or more advantages, such as that the transition to the nucleic acid amplification by the second primer set from the nucleic acid amplification by the first primer set is easier, that the nucleic acid amplification product generated by the second primer can be obtained in a large amount, and that the generation of nucleic acid amplification products is prevented from reaching a plateau due to depletion of the second primer, can also be attained.

The amount of the second primer in the reaction solution may be 1 to 400 times (by molar ratio), preferably 1 to 40 times (by molar ratio), and more preferably 1 to 20 times (by molar ratio), with respect to the amount of the primer having the largest amount among the primers constituting the first primer set. By controlling the concentration of the second primer in the reaction solution to at least be equal to the concentration of the primer having the highest concentration among the primers constituting the first primer set, it tends to be the case that, for example, the resulting amplification products can be reliably accumulated in the reaction solution without impairing the amplification efficiency and, by controlling the concentration to be no higher than 400 times, it tends to be the case that, for example, non-specific amplification is inhibited and the nucleic acid amplification reactions performed by the first primer set are not disturbed.

Further, the reaction solution may contain the third primers in such an amount that the above-described quantitative ratios with respect to the first and second primers are both satisfied. As a result, all of the above-described advantages can be attained.

Here, in the nucleic acid amplification step, the lengths of the primers included in the respective primer sets may be the same or different.

As the method of nucleic acid amplification, a method utilizing a polymerase is preferably employed, and examples of such a method include the PCR method, ICAN method, LAMP method and NASBA method. In cases where amplification is performed by a method utilizing a polymerase, it is preferred that the amplification be performed in the presence of the probes that are described below. Those skilled in the art would be able to easily adjust the amplification reaction conditions and the like in accordance with the probes and polymerase that are employed.

Further, as a DNA polymerase to be used in the PCR method, any conventionally used DNA polymerase may be selected with no particular restriction. Examples of such DNA polymerases include GENE TAQ (manufactured by Nippon Gene Co., Ltd.), PRIME STAR MAX DNA POLYMERASE (manufactured by Takara Bio Inc.) and Taq polymerases.

The amount of the polymerase to be used is not particularly restricted as long as it is used at an ordinary concentration. For example, in cases where a Taq polymerase is employed, it is preferred that the concentration thereof is from 0.01 U to 100 U with respect to 50 μl of the reaction solution.

The heating temperature for dissociation of the PCR amplification products (dissociation step) is not particularly restricted as long as it is a temperature at which the amplification products can be dissociated. For example, the heating temperature is from 85° C. to 95° C. The heating time is not particularly restricted either, and it is usually from 1 second to 10 minutes, and preferably from 1 second to 5 minutes.

Further, hybridization between the dissociated single-stranded nucleic acids and the respective primers can be performed by, for example, after the dissociation step, lowering the heating temperature of the dissociation step. This temperature is, for example, from 50° C. to 80° C.

Regarding the temperature conditions, multiple conditions may be set in the reaction process of nucleic acid amplification. For example, in nucleic acid amplification where 50 cycles of PCR reactions are performed, the reaction conditions may be adjusted such that the first 10 cycles are performed at 55° C. and the remaining 40 cycles are performed at 65° C.

The volume and concentration of the respective compositions contained in the reaction solution used in the hybridization step are not particularly restricted. Specifically, regarding the concentrations of the primers in the reaction solution, for example, the concentrations of the first primers and of the third primers are from 0.001 μM to 1 μM, and preferably from 0.01 μM to 0.5 μM, and the concentration of the second primer is, for example, from 0.01 to 10 μM, and preferably from 0.05 to 5 μM.

In order to effectively detect the signals in the signal detection step, which is described below, the reaction solution may also contain at least two types of detection probe that recognize each of the at least two types of amplification product.

The detection probes are not particularly restricted as long as they can detect the amplification product of interest. The length of the respective detection probes is not particularly restricted either; however, it is preferably from 5 mer to 50 mer, and more preferably from 10 mer to 30 mer. As long as the length of the respective detection probes is in this range, the detection sensitivity can be improved, for example.

The detection probes have a sequence with an identity of preferably from 70 to 100%, and particularly preferably not less than 80%, to the nucleic acid sequence of the corresponding gene of interest.

Further, in cases where the detection probes are allowed to coexist with the primers in the nucleic acid amplification step, in order to prevent the DNA polymerase from reacting with the detection probes and causing extension of the detection probes, it is preferred that the detection probes are added with a fluorescent label, as described below, on the 3'-end side or a phosphate group at the 3'-end.

From the standpoint of the detection efficiency, it is preferred that the detection probes are labeled probes having a labeling substance.

Specific examples of the labeling substance in the labeled probes include fluorescent dyes and fluorophores and specific preferred examples of the labeled probes include probes that are labeled with a fluorescent dye and emit fluorescence by themselves and whose fluorescence is decreased (e.g., quenched) upon formation of a hybrid.

Probes utilizing this kind of fluorescence quenching phenomenon are generally referred to as "fluorescence quenching probes". Thereamong, as the detection probes, those in which a base in the 3'-region (e.g., 3'-end) or the 5'-region (e.g., 5'-end) of the oligonucleotide is labeled with a fluorescent dye are preferred, and it is preferred that the base to be labeled is cytosine (C). In this case, in the detection target sequences to which the labeled probes hybridize, it is preferred that the base sequence of the respective labeled probes are designed such that the base forming a pair with the terminal base C of the labeled probe or a base which is positioned at 1 to 3 bases away from the base forming a pair, is guanine (G). Such a probe is generally referred to as a "guanine quenching probe" and is known as a "Q Probe".

When this kind of guanine quenching probe hybridizes to a detection target sequence, the terminal cytosine (C) labeled with a fluorescent dye approaches the guanine (G) in the detection target sequence, resulting in the phenomenon of decreased fluorescence of the fluorescent dye (decrease in the fluorescence intensity). By using such a probe, hybridization and dissociation can be easily verified based on the signal fluctuation. Further, the labeled substance is usually, for example, capable of binding to a phosphate group of a nucleotide.

In addition to this kind of detection method where a Q Probe is used, any known detection method may be applied, and examples thereof include Taq-Man Probe methods and RFLP methods.

The fluorescent dye is not particularly restricted and examples thereof include fluoresceins, phosphors, rhodamines and polymethine dye derivatives. Examples of commercially available fluorescent dyes include BODIPY FL, FluorePrime, Fluoredite, FAM, Cy3, Cy5 and TAMRA. In the present invention, since the sample solution contains multiple genes to be measured, multiple detection probes are employed. In this case, the combination of fluorescent dyes that may be preferably used in the multiple probes is not particularly restricted as long as, for example, the fluorescent dyes can be detected under different conditions, and one example of such a combination of fluorescent dyes is a combination of Pacific Blue (detection wavelength: 445 nm to 480 nm), TAMRA (detection wavelength: 585 nm to 700 nm) and BODIPY FL (detection wavelength: 520 nm to 555 nm). In cases where the multiple probes are labeled with the same fluorescent dye, it is preferred that detection probes having different Tm values with respect to the detection subject are selected.

Further, in cases where the detection probes are labeled with a labeling substance such as a fluorescent dye, in order to adjust the signal intensity to be detected such as fluorescence intensity, for example, an unlabeled probe having the same sequence as the labeled probe may also be used in combination. In this unlabeled probe, for example, a phosphate group may be added to the 3'-end.

The ratio (molar ratio) of the added detection probes to the nucleic acids in the reaction solution is not particularly restricted. The ratio is preferably not higher than 1-fold, and more preferably not higher than 0.1-fold, with respect to the amount of the nucleic acids in the sample. As a result, for example, a sufficient detection signal can be ensured.

The ratio of the added detection probes to the nucleic acids may be expressed in terms of, for example, a molar ratio with respect to double-stranded nucleic acids or a molar ratio with respect to single-stranded nucleic acids.

The abundance measurement step includes: detecting signals corresponding to the abundances of the at least two types of amplification product; and determining the abundances of the at least two genes based on the thus detected signals.

The abundances of the at least two types of amplification product reflect the abundances of the respective at least two genes; therefore, by measuring the signals corresponding to the abundances of the amplification products obtained in the nucleic acid amplification step, the abundances of the genes in nucleic acids contained in a subject sample can be determined.

The abundances of the respective genes can be determined by obtaining the detection signals of the respective amplification products (hereinafter, referred to as "the signal detection step") and then comparing the thus obtained detection signals (hereinafter, referred to as "the signal comparison step").

The detection of signals can be performed by any method which measures the abundances of the amplification products accumulated in the reaction solution, and the type of signal is not particularly restricted.

In the signal detection step, a detection method can be preferably employed in which a detection probe capable of detecting an amplification product of interest is used.

The signal comparison step includes determining the abundances of the respective genes by comparing the detection signals obtained in the signal detection step that correspond to each of the genes. The method of comparing the detection signals and the method of determining the abundances of the respective genes based on the results of the comparison are not particularly restricted.

For example, the abundances of the genes may be calculated by comparing the detection signals that correspond to each of the genes based on the relationship between the number of PCR cycles and the accumulated amount of the respective amplification products.

In this case, the amounts of the respective amplification products of the multiple genes of interest contained in the reaction solution are sequentially measured as the number of PCR cycles increases and, from the thus obtained measurement results, the abundances of the genes of interest can be determined. Generally speaking, the amount of an amplification product increases exponentially as the number of PCR cycles increases; however, in an ordinary detection method, PCR cycles are divided into an initial cycle phase in which an amplification product cannot be detected; an amplification phase in which the amount of amplification product increases exponentially and can be detected; and a plateau phase in which the reaction rate decreases. In the nucleic acid amplification step, since the multiple amplification products corresponding to each type of gene of interest are all produced by the second primer, even when the PCR cycle reaches the plateau phase, the amplification products are accumulated in the reaction solution at amount ratios that correspond to the abundances of the respective genes of interest. Therefore, by applying a means for discriminating between the types of the amplification products, the amplification products that are derived from the genes of interest and accumulated in the reaction solution can be discriminated and the ratio of their amounts can be measured, whereby the abundance of the respective genes of interest can be determined.

Examples of the means for discriminating between the types of the amplification products include Tm values of the detection probes, labeling species and DNA microarrays on which a probe(s) is immobilized.

Further, in cases where the genes of interest include a reference gene and a target gene, the abundance of the target gene may be determined based on the ratio of the amount of the target gene to that of the reference gene. In cases where the genes of interest are a 5'-gene region and a 3'-gene region of a fusion gene, the abundance of the 3'-gene region may be determined based on the ratio thereof to the abundance of the 5'-gene region or, alternatively, the abundance of the 5'-gene region may be determined based on the ratio thereof to the abundance of the 3'-gene region.

Further, the abundance measurement step may be a process in which the abundances of the at least two genes are determined by performing Tm analysis for at least two detection signals corresponding to the respective genes. In this case, it is more preferable that the signal detection and signal comparison steps include the following steps (I) to (IV). It is noted here that the following step (I) may also be performed simultaneously with the nucleic acid amplification step.

(I) A step of bringing the detection probes into contact with the single-stranded nucleic acids (amplification products) in the sample to obtain hybrids ("the hybridization step").

(II) A step of dissociating the hybrids by changing the temperature of the sample containing the hybrids so as to measure changes in the respective detection signals caused by the dissociation of the hybrids ("the measurement step").

(III) A step of detecting the Tm values (dissociation temperatures) of the hybrids based on the above-described changes in the respective detection signals ("the Tm value detection step").

(IV) A step of detecting the presence or the abundance ratios of the respective amplification products of interest in the single-stranded nucleic acids contained in the sample based on the Tm values ("the abundance ratio detection step").

In the hybridization step, the detection probes and the single-stranded nucleic acids in the sample are brought into contact and hybridized with each other. The single-stranded nucleic acids in the sample can be prepared, for example, by dissociating the amplification products obtained in the above-described manner.

The heating temperature in the dissociation of the amplification products (the dissociation step) is not particularly restricted as long as it is a temperature at which the amplification products can be dissociated. For example, the heating temperature is from 85° C. to 95° C. The heating time is not particularly restricted either, and it is usually from 1 second to 10 minutes, and preferably from 1 second to 5 minutes.

Hybridization between the thus dissociated single-stranded nucleic acids and the detection probes can be performed by, for example, after the dissociation step, lowering the heating temperature of the dissociation step. This temperature is, for example, from 25° C. to 50° C. The volume and concentration of the respective components that are contained in the reaction solution used in the hybridization step are not particularly restricted, and any conditions that are normally used can be adopted.

In the measurement step, the thus formed hybrids between the single-stranded nucleic acids and the respective detection probes are slowly heated in order to measure changes in the fluorescent signals associated with the temperature increase. For example, in cases where a Q Probe is employed, when the probe is hybridized with a single-stranded nucleic acid, the fluorescence intensity is decreased (or quenched) as compared to when the probe is in a dissociated state. Therefore, for example, hybrids with a decreased (or quenched) fluorescence may be slowly heated to measure the increase in the fluorescence intensity associated with the temperature increase.

The temperature range where the change in the fluorescence intensity is measured is not particularly restricted; however, the initial temperature is, for example, from room temperature to 85° C., and preferably from 25° C. to 70° C., and the final temperature is, for example, from 40° C. to 105° C. Further, the rate of temperature increase is not particularly restricted; however, it is, for example, from 0.1° C./second to 20° C./second, and preferably from 0.3° C./second to 5° C./second.

In the measurement step, it is preferable that the signals that are used to determine the abundances of the at least two genes are obtained in terms of the absorbance or fluorescence value measured at the same wavelength. As a result, the abundances of the genes of interest can be determined with simplified measurements and detections. In order to obtain the absorbance or fluorescence value at the same wavelength, the detection probes may be labeled with the same label, for example. In this case, from the standpoint of the detection sensitivity, it is more preferable that the primers used have different Tm values.

In the Tm detection step, the Tm value is determined by analyzing the changes in the signals. Specifically, the Tm value can be determined by calculating differential values from the measured fluorescence intensity at each temperature (−d(fluorescence Intensity)/dt) and taking the temperature showing the lowest differential value as the Tm value. Alternatively, the Tm value can also be determined as a temperature at which the increase in the fluorescence intensity per unit time (increase in the fluorescence intensity/t) has the largest value. Meanwhile, in cases where probes whose signal intensity is increased by hybrid formation, rather than quenching probes, are employed as the labeled probes, the Tm value can be determined by measuring the decrease in the fluorescence intensity.

Further, instead of heating the hybrids and measuring the changes in the fluorescence signals (preferably an increase in the fluorescence intensity) associated with the temperature increase, the changes in the signals may alternatively be measured during hybrid formation, for example. In other words, during the process of forming hybrids by lowering the temperature of the sample to which the probes have been added, changes in the fluorescence signals associated with the temperature decrease may be measured.

Specifically, in cases where a fluorescently-labeled probe (e.g., a Q Probe) is employed whose fluorescence is decreased (quenched) when it is hybridized to its complementary sequence as compared to when it is not hybridized to its complementary sequence, since the probe is in a dissociated state when added to the sample, its fluorescence intensity is high; however, the fluorescence intensity is decreased (or quenched) when a hybrid is formed by lowering the temperature of the sample. Therefore, for example, the decrease in the fluorescence intensity associated with a decrease in temperature may be measured by slowly cooling the heated sample.

Meanwhile, in cases where a labeled probe whose signal is increased by hybrid formation is employed, since this kind of probe is in a dissociated state when added to the sample, its fluorescence intensity is low (or quenched); however, the fluorescence intensity is increased when a hybrid is formed by lowering the temperature of the sample. Therefore, for example, the increase in the fluorescence intensity associated with a decrease in temperature may be measured by slowly lowering the temperature of the sample.

In the abundance ratio detection step, the abundances of the respective amplification products of interest in the single-stranded nucleic acids contained in the sample are detected based on the Tm values so as to determine the abundances of the respective genes of interest from the detected abundances.

The detection signals of the amplification products obtained in the signal detection step contain a mixture of signals for multiple amplification products derived from the multiple genes of interest. These signals reflect the abundance of the respective amplification products; therefore, by comparing the detection signals, the abundances of the genes of interest, that is, the abundances of the genes of interest in nucleic acids contained in a subject sample, can be determined. In particular, in cases where the genes of interest include the reference gene whose abundance is already known and the target gene, the abundance of the target gene can be conveniently determined based on the detection signal of the reference gene.

Further, in cases where the genes of interest are a 5′-gene region and a 3′-gene region of a fusion gene, the presence of the fusion gene in a sample can be conveniently detected by comparing the detection signal of the 5′-gene region with that of the 3′-gene region.

The method of determining the abundances of the genes based on detection signals is not particularly restricted, and any method can be employed as long as it is an analytical method which can be used for this purpose.

For example, a method in which the abundances of the genes are determined by comparing the melting curves obtained by Tm analysis of signals is preferred since it has the advantage that the abundances of the genes of interest can be accurately and simply determined, for example.

Preferred examples of this kind of Tm analysis method include those methods disclosed in WO2009/081965, WO2010/001969 and the like.

As a preferred example of the TM analysis method, a method in which the genes of interest are a reference gene and a target gene and their abundances in nucleic acids contained in a subject sample are determined by areal analysis of the results of Tm analysis, is described below.

Figure 1B:
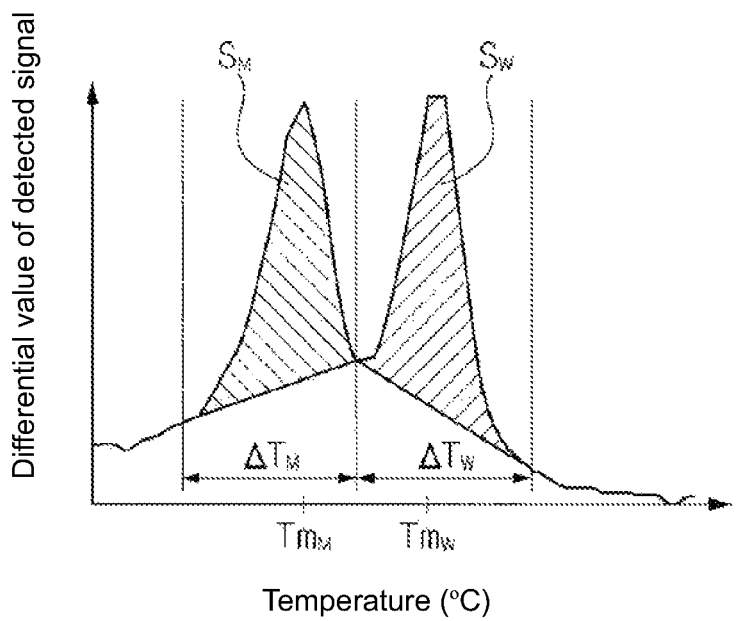

FIG. 1(A) shows a melting curve which represents the relationship between the temperature of an arbitrary nucleic acid mixture of a target gene and a reference gene and a detection signal such as absorbance or fluorescence intensity, and FIG. 1(B) shows a melting curve (also referred to as a "differential melting curve") which represents the relationship between the temperature and the differential detection signal value. By examining the peaks in this differential melting curve, the melting temperature of the nucleic acid (R) of the reference gene, $Tm_R$, and that of the nucleic acid (T) of the target gene, $Tm_T$, are determined in order to define temperature ranges including $Tm_R$ or $Tm_T$.

The temperature range $\Delta T_R$, which includes $Tm_R$, may be defined as, for example, a temperature range in which the lower limit is a temperature at which the differential detection signal value between $Tm_R$ and $Tm_T$ is minimized and the upper limit is a temperature which corresponds to the foot of the detection signal peak. Further, the temperature range $\Delta T_T$, which includes $Tm_T$, may be defined as, for example, a temperature range in which the upper limit is a temperature at which the differential detection signal value between $Tm_R$ and $Tm_T$ is minimized and the lower limit is a temperature which corresponds to the foot of the detection signal peak.

Here, the temperature ranges $\Delta T_R$ and $\Delta T_T$ may be set to have the same width (for example, 10° C.) or different widths (for example, the temperature range $\Delta T_R$ is 10° C. and the temperature range $\Delta T_T$ is 7° C.). Alternatively, the temperature ranges $\Delta T_R$ and $\Delta T_T$ may be set to have a width of ±X° C. from the respective melting temperatures (Tm) (wherein, X is, for example, 15 or less, and preferably 10 or less).

Then, for each of the temperature ranges $\Delta T_R$ and $\Delta T_T$, the area enclosed by a straight line passing through the points corresponding to the lower and upper limits of the temperature range and the differential melting curve is determined. A specific example of the method of determining the area is as follows. The area is determined using the following Equation (1), wherein f(T) is a differential detection signal value at temperature (T) and B(T) is a base value at temperature (T).

$$\text{Area}(S) = \{f(T_{s+1}) - B(T_{s+1})\} + \{f(T_{s+2}) - B(T_{s+2})\} + \ldots + \{f(T_{e-1}) - B(T_{e-1})\} \quad (1)$$

In the Equation (1), $T_s$ and $T_e$ are the lower and upper limit values of each temperature range, respectively. The base value B(T) at temperature (T) is a value determined by the following Equation (2) and represents the background level of the detection signal. By subtracting this base value from the differential detection signal value, the influence of the background included in the detection signal is eliminated.

$$B(T)=a\times(T-T_s)+f(T_s) \quad (2)$$

(wherein, $a=\{f(T_e)-f(T_s)\}/(T_e-T_s)$)

In accordance with Equations (1) and (2), for each of the nucleic acids, the area $S_R$ in the temperature range $\Delta T_R$ and the area $S_T$ in the temperature range $\Delta T_T$ are determined to calculate the relationship between the area ratio and the abundance ratio of the respective nucleic acids. For example, the abundance ratio (the ratio of the target gene T with respect to the total amount of the nucleic acids) may be plotted on the abscissa and the area ratio ($S_T/S_R$) may be plotted on the ordinate. The area ratio may be defined as $S_R/S_T$.

Here, since the abundance of the reference gene is known in advance, the abundance of the target gene can be determined by comparing the area for the reference gene and the area for the target gene.

Alternatively, the target gene may be quantified by preparing a calibration curve for a gene of interest whose specific abundance is known in advance as described above.

The abundances of multiple genes of interest are determined by using a calibration curve prepared in the above-described manner. As for the measurement of the abundances, the abundance of one of the genes of interest may be obtained relative to the abundance of the other gene by comparison. Alternatively, the specific abundance of one of the genes of interest may be determined based on the specific abundance of the other gene. In cases where one of the genes is a reference gene, the abundance of the target gene can be determined in terms of relative amount based on the abundance of the reference gene or in terms of specific amount. In cases where the abundance is determined in terms of copy number, the copy number of the target gene can be determined by comparing the detection signal of the amplification product derived from the reference gene and that of the amplification product derived from the target gene.

Here, too, in cases where the genes of interest are a 5'-gene region and a 3'-gene region, the presence of a fusion gene in a sample can be detected by comparing the detection signal of the amplification product derived from the 5'-gene region and that of the amplification product derived from the 3'-gene region in the same manner as described above.

<Gene Measurement Kit>

The gene measurement according to the present invention is a kit for use in the above-described gene measurement method and includes the first primer set, which includes the first primers, and the second primer.

By using the measurement kit according to the present invention, the abundances of genes of interest having different abundances can be simply determined Further, the measurement kit may also include the third primers in addition to the first and second primers.

With regard to the first, second and third primers that are included in the gene measurement kit according to the present invention, those matters described above are applied without modification.

Further, the measurement kit may also include at least two detection probes, each of which has a base sequence capable of hybridizing to the region to be amplified of the at least two genes and contains a label. As a result, with the use of the detection probes, the abundances of the genes of interest having different abundances can be determined even more simply. As the detection probes to be included in the measurement kit, those in which the label is a fluorescent label are preferred. With regard to the label and fluorescent label, those matters described above are applied without modification.

In addition to the probes, the measurement kit may further include a reagent(s) required for performing the nucleic acid amplification in the measurement method according to the present invention. The probes, primers and other reagent(s) may be contained separately, or some of them may be contained in the form of a mixture.

Here, the condition "contained separately" may be any condition in which the reagents are separated from each other such that they can maintain a non-contact state, and it is not necessarily required that the reagents are housed in separate containers that can be handled independently.

Further, it is preferred that the measurement kit according to the present invention also include an instruction manual that provides instructions for preparing a differential melting curve for a sample containing the genes of interest by using the first primer set, which includes the first primers, and the second primer and for performing Tm value analysis of the resulting differential melting curve so as to determine the abundances of the genes of interest, or a user's manual that describes various reagents that are included or may be additionally included in the measurement kit.

Further, the measurement kit according to the present invention may be used for detecting a fusion gene mutation. Examples of an ALK fusion gene measurement kit include a measurement kit that includes the first primer set, which includes first primers capable of amplifying a specific gene region of the ALK gene (for example, SEQ ID NOs:19 and 21), and a second primer (for example, SEQ ID NO:22). Moreover, the ALK fusion gene measurement kit may include the first primer set, which includes first primers capable of amplifying a specific gene region of the ALK gene (for example, SEQ ID NOs:19 and 21), a second primer (for example, SEQ ID NO:22) and third primers (for example, SEQ ID NOs:18 and 20).

<Gene Measuring Apparatus>

The gene measuring apparatus according to the present invention is an apparatus to which the above-described method of measuring the gene abundance can be applied. The gene measuring apparatus includes a detection unit that detects at least two signals corresponding to the abundances of the amplification products containing the single additional base sequence introduced by the first primers and corresponding to the at least two genes amplified by the second primer; and an arithmetic unit that calculates the abundances of the at least two genes by comparing the detection signals of the at least two genes that are detected by the detection unit.

By using this gene measuring apparatus, the method of measuring the gene abundance according to the present invention can be carried out more simply.

The detection unit is not particularly restricted as long as it can detect the detection signals. The detection unit can be selected as appropriate in accordance with, for example, the type of detection signal. For example, in cases where the detection probes are fluorescently-labeled probes, the detection unit can include a fluorescence detector.

The arithmetic unit calculates the abundances of the respective genes of interest in the reaction solution based on the detection signals detected by the detection unit.

The calculation process includes, for example, differentiating detection signals of a melting curve with respect to temperature to obtain a differential melting curve representing the relationship between the temperature and the differential value of the detection signals; defining temperature ranges, which were set in advance in the preparation of a calibration curve, in the thus obtained differential melting curve; determining the areas corresponding to the respective genes of interest, each area being enclosed by a straight line passing through the points corresponding to the lower and upper limits of each temperature range and the differential melting curve; calculating the ratio of the thus determined areas; and, based on the calibration curve prepared in advance, calculating the abundance ratio of the genes of interest corresponding to the thus calculated area ratio.

As the apparatus containing a detection unit and an arithmetic unit, any known apparatus may be employed. For example, those apparatuses disclosed in WO2009/081965, WO2010/001969 and the like may be employed without any modification.

<Gene Measuring System>

The gene measuring system according to the invention is an apparatus to which the above-described method of measuring the gene abundance can be applied. The gene measuring system includes a detection device that detects at least two signals corresponding to the abundances of the amplification products containing the single additional base sequence introduced by the first primers and corresponding to the at least two genes amplified by the second primer; and an arithmetic device that calculates the abundances of the at least two genes by comparing the detection signals of the at least two genes that are detected by the detection device.

By using this gene measuring system, the method of measuring the gene abundance according to the present invention can be carried out more simply.

As the detection device and arithmetic device that are used in this system, those described above as the detection unit and arithmetic unit of the gene measuring apparatus can be employed without any modification.

Further, in the same manner as for the above-described measuring apparatus, with regard to the detection device and arithmetic device, those devices disclosed in WO2009/081965, WO2010/001969 and the like may be applied without any modification, for example.

<Gene Diagnosis Method>

The gene diagnosis method according to the present invention is a diagnostic method performed by using the gene measurement method.

According to this method, based on the abundances of at least two genes having different abundances in nucleic acids contained in a subject sample, diseases, drug metabolic capacity, drug sensitivity and the like that are associated with gene abundance can be diagnosed.

Preferably, the abundances of the genes of interest are determined in terms of copy number and the present invention is applied to diagnosis of copy number polymorphism where variation in the copy number in nucleic acids contained in a subject sample is used as an index. Examples of such diseases where copy number polymorphism is used as an index for diagnosis include neuroblastoma caused by copy number polymorphism in the chromosome 1q21.1. According to the present invention, the abundance of a gene associated with such diseases, drug metabolic capacity or drug sensitivity can be determined and diagnosed with good accuracy.

EXAMPLES

The present invention will now be described in detail by way of examples thereof. However, the present invention is not in any way restricted to the following examples. It is noted here that, unless otherwise specified, all "%" are by mass.

Example 1

The abundance of a specific sequence region of a human CYP2D6 gene (SEQ ID NO:1) was measured using the CYP2D6 gene as a target gene. As a reference gene, a specific sequence region of a human sod2 gene (SEQ ID NO:2) was employed. The genomic sequences of the CYP2D6 gene and the sod2 gene are available as GenBank NG008376 and GenBank NG008729, respectively.

Artificial nucleic acids (plasmids) were prepared by inserting the base sequence shown in SEQ ID NO:1 or SEQ ID NO:2 into pUC57 and, in order to obtain varied copy numbers of the CYP2D6 gene, samples a to d containing various plasmid solutions were prepared as shown in Table 1. Using the thus prepared plasmid solutions, various samples (various templates) each containing the target and reference genes at prescribed copy numbers were prepared.

TABLE 1

|   | 2D6-Int6 (copies/µL) | sod2 (copies/µL) |
|---|---|---|
| a | 125 | 250 |
| b | 250 | 250 |
| c | 375 | 250 |
| d | 500 | 250 |

Using a fully-automated SNP analyzer (trade name: I-DENSY (trademark); manufactured by ARKRAY, Inc.) and reagents having the formulation shown in Table 3, including the various probes and primers shown in Table 2 below, PCR and Tm analysis were carried out. Here, as the polymerase, a Taq polymerase was employed.

The PCR was performed by treating the sample at 95° C. for 60 seconds and then repeating 60 cycles of 95° C. for 1 second and 63° C. for 15 seconds.

Tm analysis was performed after the PCR by treating the sample at 95° C. for 1 second and then at 40° C. for 60 seconds and subsequently measuring the change in fluorescence intensity over time during a period in which the temperature of the resultant sample was increased from 40° C. to 80° C. at a rate of 1° C./3 seconds. The excitation wavelength and the measurement wavelength were set at from 520 nm to 555 nm and from 585 nm to 700 nm, respectively, to measure the changes in the fluorescence intensity derived from the respective fluorescently labeled probes. Here, the target gene (CYP2D6) and the reference gene (sod2) are known to exhibit a peak at about 58° C. and at about 70° C., respectively.

Figure 2A:
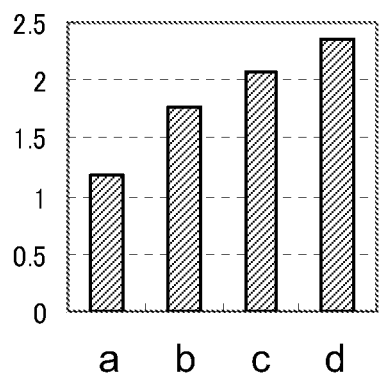
FIG. 2A is a graph showing the results of Tm analyses according to Example 1 of the present invention.

Tm value-based analysis was performed based on areal analysis. Specifically, for each of samples a to d, a differential melting curve was prepared from the results of the Tm analysis, and the Tm value and the area of each of the target gene and the reference gene were obtained to determine the ratio of the thus obtained area of the target gene to that of the reference gene. The results are shown in Table 8 and FIG. 2A.

The sequences of the respective primers and probes that were used are shown in Table 2.

The nucleic acid sequence of the CYP2D6 gene was amplified using a first primer (SEQ ID NO:3, Tm value=70.4° C.) consisting of a single additional base sequence and the base sequence complementary to a base sequence characteristic of the CYP2D6 gene, and a third primer (SEQ ID NO:4, Tm value=55.7° C.) consisting of the base sequence complementary to a base sequence characteristic of the CYP2D6 gene. The nucleic acid sequence of the sod2 gene was amplified using a first primer (SEQ ID NO:6, Tm value=69.7° C.) consisting of the above-described single additional base sequence and the base sequence complementary to a base sequence characteristic of the sod2 gene, and a third primer (SEQ ID NO:5, Tm value=57.3° C.) consisting of a base sequence corresponding to a base sequence characteristic of the sod2 gene. Then, the resulting amplification products were each amplified using a second primer (SEQ ID NO:7, Tm value=59.6° C.) consisting of only the above-described single additional base sequence, and the respective third primers. The CYP2D6 detection probe (SEQ ID NO:8) and the sod2 detection probe (SEQ ID NO:9) are as shown in Table 2. The Tm values of the respective primers were calculated using the MeltCalc software.

It is noted here that, in Table 2, those base sequences that are indicated with lower case letters represent the single additional base sequence.

TABLE 2

| Name | Sequence (5' → 3') | mer | SEQ ID | Tm (° C.) | Note |
|---|---|---|---|---|---|
| 2D6-P3F4-Int6r-F1 | cgctgtagtcgaagacgatgtttacgTGAGCCCATCTGGGAAACA | 45 | 3 | 70.4 | First primer for CYP2D6 |
| 2D6-Int6f-R1 | GGTGTCCCAGCAAAGTTCATG | 21 | 4 | 55.7 | Third primer for CYP2D6 |
| sod2-F1 | GGAGAAGCTGACGGCTGC | 18 | 5 | 57.3 | Third primer for sod2 |
| P3F4-sod2-R3 | cgctgtagtcgaagacgatgtttacgCCTTATTGAAACCAAGCCAACC | 48 | 6 | 69.7 | First primer for sod2 |
| PEN3 F4 | cgctgtagtcgaagacgatgtttacg | 26 | 7 | 59.6 | Second primer for CYP2D6 and sod2 |
| 3T-2D6-Int6-R1 | CTGTACCCTTCCTCCC-(TAMRA) | 16 | 8 | — | CYP2D6 detection probe |
| 5T-sod2-F1-25 | (TAMRA)-CATCTGTTGGTGTCCAAGGCTCAGG-P | 25 | 9 | — | sod detection probe |

TABLE 3

| Example | 1 test |
|---|---|
| 1 × PCR buffer | |
| dNTP | 0.2 mM |
| MgCl$_2$ | 1.5 mM |
| Taq polymerase (manufactured by ARKRAY Inc.) | 1.88 U/test |
| 2D6-P3F4-Int6r-F1 | 50 nM |
| 2D6-Int6f-R1 | 100 nM |
| sod2-F1 | 100 nM |
| P3F4-sod2-R3 | 50 nM |

TABLE 3-continued

| Example | 1 test |
|---|---|
| PEN3F4 | 1000 nM |
| 3T-2D6-Int6-R1 | 100 nM |
| 5T-sod2-F1-25 | 100 nM |
| template | 4 µL |
| total | 50 µL |

Comparative Examples 1 to 3

In Comparative Example 1, PCR and Tm analysis were performed in the same manner as in Example 1, except that a primer set including, as shown in Table 4 below, primers that do not contain the single additional base sequence for both of the CYP2D6 and sod2 genes (2D6-Int6r-F1=SEQ ID NO:10; sod2-R1=SEQ ID NO:11) was employed and the reagents had the formulation shown in Table 5 in which no second primer was employed.

In Comparative Example 2, PCR and Tm analysis were performed in the same manner as in Example 1, except that the reagents had the formulation shown in Table 6 wherein a primer set including, as shown in Table 4 below, primers that do not contain the single additional base sequence for both of the CYP2D6 and sod2 genes (2D6-Int6r-F1=SEQ ID NO:10; sod2-R1=SEQ ID NO:11) was employed.

In Comparative Example 3, PCR and Tm analysis were performed in the same manner as in Example 1, except that the reagents had the formulation shown in Table 7 where the second primer (PEN3 F4=SEQ ID NO:7, see Table 2) was not employed.

Figure 2B:
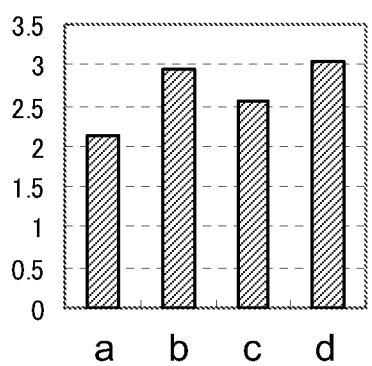
FIG. 2B is a graph showing the results of Tm analyses according to Comparative Example 1 of the present invention.
Figure 2C:
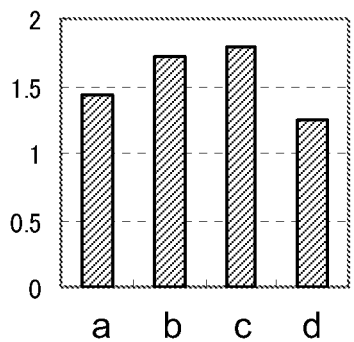
FIG. 2C is a graph showing the results of Tm analyses according to Comparative Example 2 of the present invention.
Figure 2D:
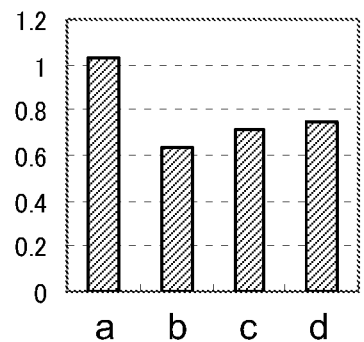
FIG. 2D is a graph showing the results of Tm analyses according to Comparative Example 3 of the present invention.

The sequences of the respective primers that were used in Comparative Examples 1 to 3 and the results of the Tm analyses are shown in Table 8 and FIGS. 2B to 2D.

TABLE 4

| Name | Sequence (5'→3') | mer | SEQ ID | Note |
|---|---|---|---|---|
| 2D6-Int6r-F1 | TGAGCCCATCTGGGAAACA | 19 | 10 | Primer for CYP2D6 |
| 2D6-Int6f-R1 | GGTGTCCCAGCAAAGTTCATG | 21 | 4 | Primer for CYP2D6 |
| sod2-F1 | GGAGAAGCTGACGGCTGC | 18 | 5 | Primer for sod2 |
| sod2-R1 | CCTTATTGAAACCAAGCCAACC | 22 | 11 | Primer for sod2 |

TABLE 5

| Comparative Example 1 | 1 test |
|---|---|
| 1 × PCR buffer | |
| dNTP | 0.2 mM |
| MgCl$_2$ | 1.5 mM |
| Taq polymerase (manufactured by ARKRAY Inc.) | 1.88 U/test |
| 2D6-Int6r-F1 | 500 nM |
| 2D6-Int6f-R1 | 100 nM |
| sod2-F1 | 100 nM |
| sod2-R1 | 500 nM |
| 3T-2D6-Int6-R1 | 100 nM |
| 5T-sod2-F1-25 | 100 nM |
| template | 4 µL |
| total | 50 µL |

TABLE 6

| Comparative Example 2 | 1test |
| --- | --- |
| 1 × PCR buffer | |
| dNTP | 0.2 mM |
| MgCl$_2$ | 1.5 mM |
| Taq polymerase (manufactured by ARKRAY Inc.) | 1.88 U/test |
| 2D6-Int6r-F1 | 50 nM |
| 2D6-Int6f-R1 | 100 nM |
| sod2-F1 | 100 nM |
| sod2-R1 | 50 nM |
| PEN3F4 | 1000 nM |
| 3T-2D6-Int6-R1 | 100 nM |
| 5T-sod2-F1-25 | 100 nM |
| template | 4 µL |
| total | 50 µL |

TABLE 7

| Comparative Example 3 | 1test |
| --- | --- |
| 1 × PCR buffer | |
| dNTP | 0.2 mM |
| MgCl$_2$ | 1.5 mM |
| Taq polymerase (manufactured by ARKRAY Inc.) | 1.88 U/test |
| 2D6-P3F4-Int6r-F1 | 50 nM |
| 2D6-Int6f-R1 | 100 nM |
| sod2-F1 | 100 nM |
| P3F4-sod2-R3 | 50 nM |
| 3T-2D6-Int6-R1 | 100 nM |
| 5T-sod2-F1-25 | 100 nM |
| template | 4 µL |
| total | 50 µL |

TABLE 8

| Sample | Example 1 | Comparative Example 1 | Comparative Example 2 | Comparative Example 3 |
| --- | --- | --- | --- | --- |
| a | 1.18 | 2.14 | 1.44 | 1.03 |
| b | 1.77 | 2.96 | 1.72 | 0.63 |
| c | 2.08 | 2.54 | 1.79 | 0.71 |
| d | 2.37 | 3.05 | 1.25 | 0.74 |

As shown in Table 8 and FIGS. 2A to 2D, in Example 1, an increase in the area ratio in accordance with the copy number of the target gene in samples a to d was observed, reflecting an increase in the copy number. In contrast, in all of Comparative Examples 1 to 3, results reflecting an increase in the copy number were not obtained as the area ratio did not correspond to an increase in the copy number in the samples.

Even when Example 1 and Comparative Example 1 were each repeated three times, the same trends were observed (data not shown).

Examples 2 and 3

In Example 2, Tm analysis was performed in the same manner as in Example 1, except that the second primer was changed to PEN3 F4+CTACG, containing the additional base sequence for adjustment (CTACGCTACGCTACGcgctg-tagtcgaagacgatgtttacg: SEQ ID NO:12, 41 mer, Tm value=69.4° C.), the reagents had the formulation shown in Table 9, and PCR was performed by treating the sample at 95° C. for 60 seconds and then repeating 50 cycles of 95° C. for 1 second and 60° C. for 15 seconds. The results are shown in Table 11 and FIG. 3.

In Example 3, PCR and Tm analysis were performed in the same manner as in Example 1, except that the first primer for the CYP2D6 gene was changed to 2D6-P3F4-Int6r-F2, in which four bases of the single additional base sequence are deleted on the 5'-end side and the base sequence of the CYP2D6 gene corresponding to the region to be amplified contains a degenerate base (gtagtcgaagacgatgtttacgTGAGC-CCATCTGGG(B)AACA, B=c, g or t: SEQ ID NO:13, 41 mer, Tm value=67.6 to 69.2° C.); the first primer for the sod2 gene was changed to P3F4-sod2-R4, in which four bases of the single additional base sequence are deleted on the 5'-end side and the base sequence of the sod2 gene corresponding to the region to be amplified contains a degenerate base (gtagtc-gaagacgatgtttacgCCTTATTGAAACCAAGC(D)AACC, D=a, g or t: SEQ ID NO:14, 44 mer, Tm value=66 to 67.3° C.); the reagents had the formulation shown in Table 10; and PCR was performed by treating the sample at 95° C. for 60 seconds and then repeating 5 cycles of 95° C. for 1 second and 57° C. for 15 seconds, followed by 45 cycles of 95° C. for 1 second and 63° C. for 45 seconds. The Tm values of the respective primers were calculated using the MeltCalc software. The results are shown in Table 11 and FIG. 4.

TABLE 9

| Example 2 | 1test |
| --- | --- |
| 1 × PCR buffer | |
| dNTP | 0.2 mM |
| MgCl$_2$ | 1.5 mM |
| Taq polymerase (manufactured by ARKRAY Inc.) | 1.88 U/test |
| 2D6-P3F4-Int6r-F1 | 50 nM |
| 2D6-Int6f-R1 | 100 nM |
| sod2-F1 | 100 nM |
| P3F4-sod2-R3 | 50 nM |
| PEN3 F4 + CTACG | 1000 nM |
| 3T-2D6-Int6-R1 | 100 nM |
| 5T-sod2-F1-25 | 100 nM |
| template | 4 µL |
| total | 50 µL |

TABLE 10

| Example 3 | 1test |
| --- | --- |
| 1 × PCR buffer | |
| dNTP | 0.2 mM |
| MgCl$_2$ | 1.5 mM |
| Taq polymerase (manufactured by ARKRAY Inc.) | 1.88 U/test |
| 2D6-P3F4-Int6r-F2 | 200 nM |
| 2D6-Int6f-R1 | 200 nM |
| sod2-F1 | 200 nM |
| P3F4-sod2-R4 | 200 nM |
| PEN3 F4 | 1000 nM |
| 3T-2D6-Int6-R1 | 100 nM |
| 5T-sod2-F1-25 | 100 nM |
| template | 4 µL |
| total | 50 µL |

TABLE 11

| Sample | Example 2 | Example 3 |
| --- | --- | --- |
| a | 0.25 | 1.45 |
| b | 0.44 | 2.11 |
| c | 0.73 | 3.59 |
| d | 0.91 | 4.81 |

Figure 3:
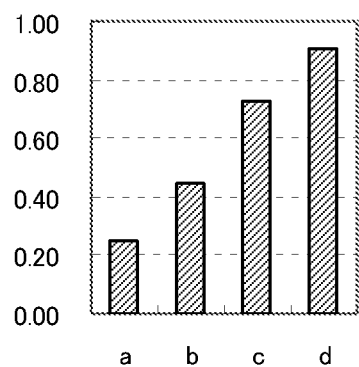
FIG. 3 is a graph showing the results of Tm analyses according to Example 2 of the present invention.
Figure 4:
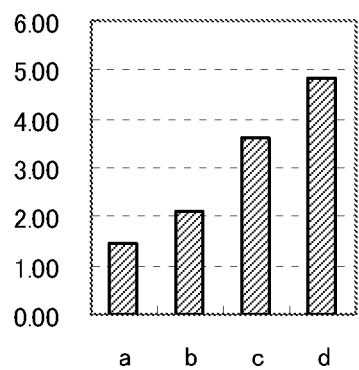
FIG. 4 is a graph showing the results of Tm analyses according to Example 3 of the present invention.

As shown in Table 11 and FIGS. 3 and 4, in Examples 2 and 3, an increase in the area ratio in accordance with the copy number of the target gene in samples a to d was observed, reflecting an increase in the copy number. In addition, by modifying the primer and reaction temperature conditions, the waveforms of the resulting detection graphs are changed and different area ratios can be obtained thereby; therefore, by appropriately modifying these conditions, the reagent formulation can be optimized.

Examples 4 and 5

In Example 4, PCR and Tm analysis were performed in the same manner as in Example 1, except that the first primers were changed to 2D6-P3F4-Int6-F2 (gtagtcgaagacgatgtt-tacgTGAGCCCATCTGGG(B)AACA: SEQ ID NO:13, 41 mer, Tm value=67.6° C. to 69.2° C.) and P3F4-sod2-R4 (gtagtcgaagacgatgtttacgCCTTATTGAAACCAAGC(D)AACC: SEQ ID NO:14, 44 mer, Tm value=66° C. to 67.3° C.), respectively, both of which contain an additional sequence for adjustment and a degenerate base; the second primer was changed to PEN3 F4+CTACG containing an additional base sequence for adjustment (CTACGCTACGC-TACGcgctgtagtcgaagacgatgtttacg: SEQ ID NO:12, 41 mer, Tm value=69.4° C.); the reagents had the formulation shown in Table 12; and PCR was performed by treating the sample at 95° C. for 60 seconds and then repeating 5 cycles of 95° C. for 1 second and 57° C. for 15 seconds, followed by 45 cycles of 95° C. for 1 second and 63° C. for 45 seconds.

In Example 5, PCR and Tm analysis were performed in the same manner as in Example 4, except that the amounts of the respective primers were changed as shown in Table 13.

Figure 5:
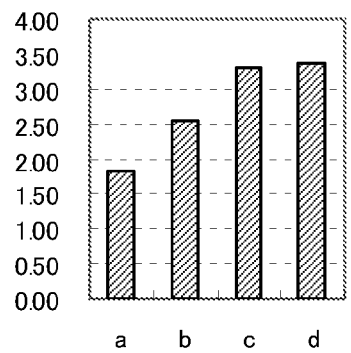
FIG. 5 is a graph showing the results of Tm analyses according to Example 4 of the present invention.
Figure 6:
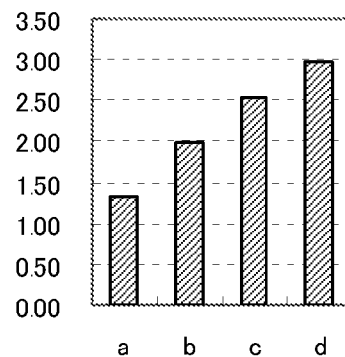
FIG. 6 is a graph showing the results of Tm analyses according to Example 5 of the present invention.

The results are shown in Table 14 and FIGS. 5 and 6.

TABLE 12

| Example 4 | 1test |
|---|---|
| 1 × PCR buffer | |
| dNTP | 0.2 mM |
| MgCl$_2$ | 1.5 mM |
| Taq polymerase (manufactured by ARKRAY Inc.) | 1.88 U/test |
| 2D6-P3F4-Int6r-F2 | 100 nM |
| 2D6-Int6f-R1 | 200 nM |
| sod2-F1 | 200 nM |
| P3F4-sod2-R4 | 100 nM |
| PEN3 F4 + CTACG | 1000 nM |
| 3T-2D6-Int6-R1 | 100 nM |
| 5T-sod2-F1-25 | 100 nM |
| template | 4 µL |
| total | 50 µL |

TABLE 13

| Example 5 | 1test |
|---|---|
| 1 × PCR buffer | |
| dNTP | 0.2 mM |
| MgCl$_2$ | 1.5 mM |
| Taq polymerase (manufactured by ARKRAY Inc.) | 1.88 U/test |
| 2D6-P3F4-Int6r-F2 | 200 nM |
| 2D6-Int6f-R1 | 100 nM |
| sod2-F1 | 100 nM |
| P3F4-sod2-R4 | 200 nM |
| PEN3 F4 + CTACG | 1000 nM |

TABLE 13-continued

| Example 5 | 1test |
|---|---|
| 3T-2D6-Int6-R1 | 100 nM |
| 5T-sod2-F1-25 | 100 nM |
| template | 4 µL |
| total | 50 µL |

TABLE 14

| Sample | Example 4 | Example 5 |
|---|---|---|
| a | 1.81 | 1.32 |
| b | 2.56 | 1.99 |
| c | 3.30 | 2.54 |
| d | 3.38 | 2.98 |

As shown in Table 14 and FIGS. 5 and 6, in Examples 4 and 5, an increase in the area ratio in accordance with the copy number of the target gene in samples a to d was observed, reflecting an increase in the copy number.

In Example 4, a second primer having a higher Tm value than that of the first primers was employed and the first primers were each used in a smaller amount than the respective third primers. In Example 5, the same combination of primers as in Example 4 was employed and the first primers were each used in a larger amount than the respective third primers. In both of these cases, as shown in Table 14 and FIGS. 5 and 6, the results obtained appropriately reflected an increase in the copy number of the target gene.

Examples 6 to 8

In Examples 6 to 8, PCR and Tm analysis were performed in the same manner as in Example 1, except that the probe for the CYP2D6 gene was changed to 3T-2D6-Int6-R2 (gtaccct-tcctccc-(TAMRA); SEQ ID NO:15) and the reagents had the formulation shown in Table 15 in which the amount of the second primer (PEN3 F4) was changed to 100 nm (Example 6), 400 nM (Example 7) or 1,200 nM (Example 8).

Figure 7:
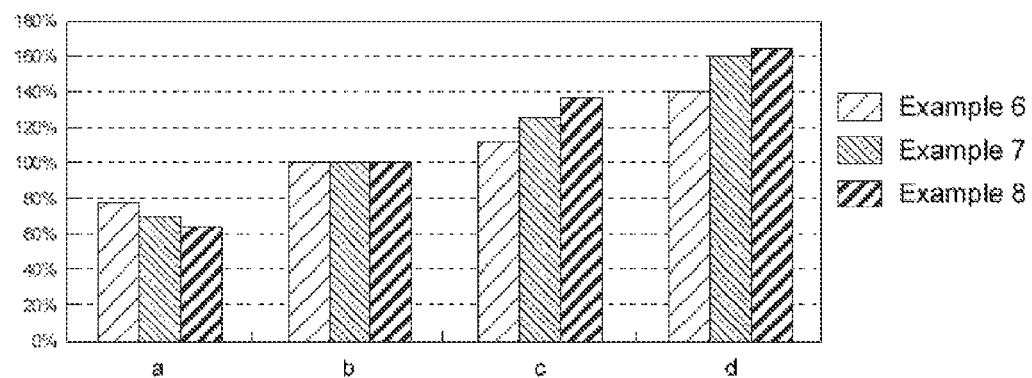
FIG. 7 is a graph showing the results of Tm analyses according to Examples 6 to 8 of the present invention.

The results are shown in Table 16 and FIG. 7. It is noted here that, in FIG. 7, the area ratios in the respective samples according to Examples 6 to 8 are represented in terms of percentage, taking the area ratio at a target gene (CYP2D6) amount of 250 copies/µL as 100%.

TABLE 15

| Example 6~8 | 1test |
|---|---|
| 1 × PCR buffer | |
| dNTP | 0.2 mM |
| MgCl$_2$ | 1.5 mM |
| Taq polymerase (manufactured by ARKRAY Inc.) | 1.88 U/test |
| 2D6-P3F4-Int6r-F1 | 100 nM |
| 2D6-Int6f-R1 | 100 nM |
| sod2-F1 | 100 nM |
| P3F4-sod2-R3 | 100 nM |
| PEN3F4 | 100 nM/400 nM/1200 nM |
| 3T-2D6-Int6-R2 | 100 nM |
| 5T-sod2-F1-25 | 100 nM |
| template | 4 µL |
| total | 50 µL |

TABLE 16

| Sample | Example 6 | Example 7 | Example 8 |
|---|---|---|---|
| a | 0.40 | 0.33 | 0.45 |
| b | 0.51 | 0.48 | 0.71 |
| c | 0.57 | 0.60 | 0.97 |
| d | 0.71 | 0.77 | 1.17 |

As shown in Table 16 and FIG. 7, in Examples 6 to 8, even when the amount of the second primer in the reaction solution was changed, an increase in the area ratio in accordance with the copy number of the target gene in samples a to d was observed, reflecting an increase in the copy number.

In addition, it was found that the rate of increase in the area ratio was increased when the amount of the second primer was made larger than the amounts of other primers in the reaction solution and that the rate of increase in the area ratio was decreased when the amount of the second primer was made smaller than the amounts of other primers in the reaction solution.

In all of these cases, as shown in Table 16 and FIG. 7, the results obtained appropriately reflected an increase in the copy number of the target gene.

Therefore, according to the present invention, the abundance of a gene(s) in nucleic acids contained in a subject sample can be measured more accurately and simply as compared to conventional techniques.

Example 9

From an artificial nucleic acid (plasmid) obtained by inserting a sequence consisting of the 2,460th to 2,801st bases of NCBI Accession No. NM004304.4 (SEQ ID NO:24) and a sequence consisting of the 4,690th to 5,031st bases of NCBI Accession No. NM004304.4 (SEQ ID NO:25), which were used as a 5'-gene region and 3'-gene region of an ALK gene, respectively, into pcDNA3.1 (+), an RNA was synthesized to prepare templates having the respective copy numbers shown in Table 17.

TABLE 17

| | 3'-gene region (copies/test) | 5'-gene region (copies/test) |
|---|---|---|
| a | 10,000 | 10,000 |
| b | 20,000 | 10,000 |
| c | 100,000 | 10,000 |

Using a fully-automated SNP analyzer (trade name: I-DENSY (trademark); manufactured by ARKRAY, Inc.) and detection reagents having the formulation shown in Table 19, including the various probes and primers shown in Table 18 below, RT-PCR and Tm analysis were carried out. Here, as the polymerase, a Taq polymerase was employed. Further, PEN3 R2 (common primer) was added in an amount of 0.2 µM or 4 µM.

The sample was treated at 55° C. for 15 minutes to perform a reverse transcription reaction.

After the reverse transcription reaction, PCR was performed by treating the resulting sample at 95° C. for 60 seconds and then repeating 50 cycles of 95° C. for 1 second and 58° C. for 15 seconds.

Tm analysis was performed after the PCR by treating the sample at 95° C. for 1 second and then at 40° C. for 60 seconds and subsequently measuring the change in fluorescence intensity over time during a period in which the temperature of the resulting sample was increased from 40° C. to 75° C. at a rate of 1° C./3 seconds.

The excitation wavelength and the measurement wavelength were set at from 520 nm to 555 nm and from 585 nm to 700 nm, respectively, to measure the changes in the fluorescence intensity derived from the respective fluorescently labeled probes.

Here, the amplification product derived from the 5'-gene region and the amplification product derived from the 3'-gene region are known to exhibit a peak at about 51° C. and about 58° C., respectively.

Figure 8:
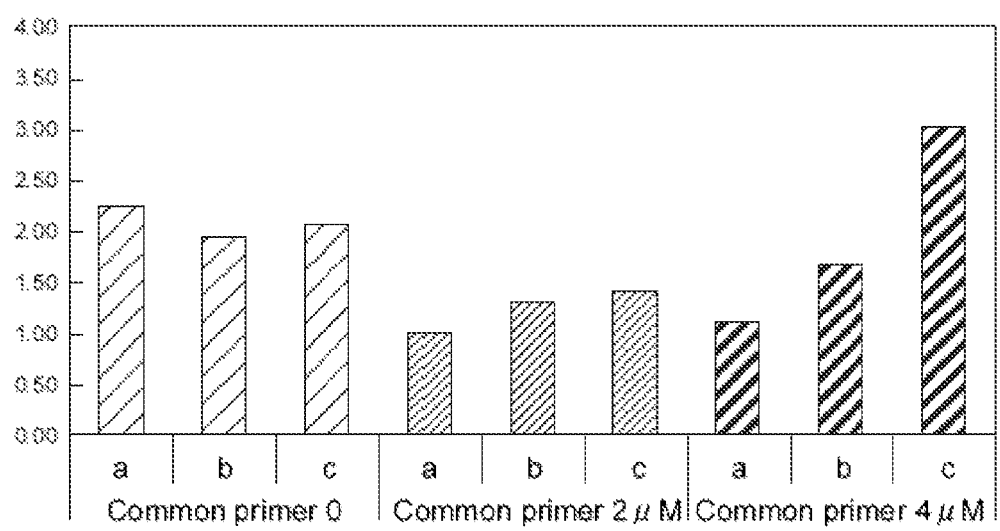
FIG. 8 is a graph showing the results of Tm analyses according to Example 9 of the present invention.

Tm value-based analysis was performed based on areal analysis. Specifically, for each of samples a to c, a differential melting curve was prepared from the results of the Tm analysis, and the Tm value and the area for each of the 5'-gene region and the 3'-gene region were obtained to determine the ratio of the thus obtained area of the 3'-gene region to that of the 5'-gene region. The results are shown in Table 20 and FIG. 8.

The sequences of the respective primers and probes that were used are shown in Table 18.

The 5'-gene region was amplified using a first primer for the 5'-gene region (P3R2-ALK5'-R5; SEQ ID NO:19, Tm value=70.5° C.) and a third primer (ALK5'-F2; SEQ ID NO:18, Tm value=59.9° C.). The 3'-gene region was amplified using a first primer therefor (P3R2-ALK3'-R3; SEQ ID NO:21, Tm value=70.1° C.) and a third primer (ALK3'-F3; SEQ ID NO:20, Tm value=60.8° C.). Then, the resulting amplification products were each amplified using a second primer (PEN3 R2; SEQ ID NO:22, Tm value=58.6° C.), which is a common primer consisting solely of the single additional base sequence, and the respective third primers.

The detection probe for the 5'-gene region (SEQ ID NO:16) and the detection probe for the 3'-gene region (SEQ ID NO:17) are as shown in Table 18.

The Tm values of the respective primers were calculated using the MeltCalc software.

It is noted here that, in Table 18, those base sequences that are indicated with lower case letters represent the single additional base sequence.

TABLE 18

| Name | Sequence(5'→3') | mer | SEQ ID |
|---|---|---|---|
| Probe | | | |
| 5T-ALK5'-F2 | (TAMRA)-CTCATTCGTGGAGTCT | 16 | 16 |
| 3T-ALK3'-F2 | GGAAGGAATATTCAC-(TAMRA) | 15 | 17 |
| Primer | | | |
| ALK5'-F2 | TCTCCATGTGAGCTCCGAATGTCC | 24 | 18 |
| P3R2-ALK5'-R5 | cgatcctgtttcttagcttagtcaagatccCCTTGCTCCTTCCCGGTTTTGTTC | 54 | 19 |
| ALK3'-F3 | GGATGCCCCCAGAGGCCTTC | 20 | 20 |
| P3R2-ALK3'-R3 | cgatcctgtttcttagcttagtcaagatccTAGCAGCACTCCAAAGGACCATGTG | 55 | 21 |
| PEN3 R2 | cgatcctgtttcttagcttagtcaagatcc | 30 | 22 |

TABLE 19

|  | 1test |
|---|---|
| 1 × PCR buffer |  |
| dNTP | 0.2 mM |
| MgCl$_2$ | 1.5 mM |
| Taq polymerase (manufactured by ARKRAY Inc.) | 1.88 U/test |
| DTT (dithiothreitol) | 2 mM |
| SUPERase·In ™ (RNase Inhibitor/Ambion) | 0.1 U/μL |
| SuperScript ™ III(reverse transcriptase; manufactured by INVITROGEN) | 0.1 U/μL |
| ALK5'-F2 | 200 nM |
| P3R2-ALK5'-R5 | 400 nM |
| ALK3'-F3 | 100 nM |
| P3R2-ALK3'-R3 | 200 nM |
| PEN3 R2 (common primer) | 0, 2 μM or 4 μM |
| 5T-ALK5'-F2 | 100 nM |
| 3T-ALK3'-F2 | 100 nM |
| template | 2 μL |
| total | 50 μL |

TABLE 20

| The added amount of common primer | Template | Area ratio |
|---|---|---|
| 0 | a | 2.24 |
|  | b | 1.94 |
|  | c | 2.05 |
| 2 μM | a | 1.01 |
|  | b | 1.31 |
|  | c | 1.42 |
| 4 μM | a | 1.12 |
|  | b | 1.68 |
|  | c | 3.00 |

Based on the results shown above, according to the present invention, the presence or absence of a fusion gene mutation can be measured inexpensively and accurately.

The disclosure of Japanese Patent Application No. 2011-238953 filed on Oct. 31, 2011 is hereby incorporated by reference in its entirety.

All the literature, patent applications and technical standards described in the present specification are hereby incorporated by reference to the same extent as in cases where each item of literature, patent application or technical standard is specifically and individually described to be incorporated by reference.

What is claimed is:

1. A method of measuring gene abundance, the method comprising:
  obtaining at least two amplification products,
    by amplifying, in one reaction solution, nucleic acids encoding at least two genes, contained in a subject sample,
    using (i) a second primer, and (ii) a first primer set, which includes at least two first primers, each of which comprises (a) a base sequence which hybridizes to the second primer or to the base sequence complementary to the second primer and (b) a sequence corresponding to each of the at least two genes; and
  calculating the abundances of the at least two genes based on detected signals corresponding to the abundances of the at least two types of amplification products.

2. The method according to claim 1, wherein the base sequence which hybridizes to the second primer or to the base sequence complementary to the second primer comprises a base sequence that is non-homologous to the base sequence in a region to be amplified of the respective nucleic acids encoding each of the at least two genes.

3. The method according to claim 1, wherein the first primer set comprises the first primers and third primers, the third primers amplifying a base sequence in the strand complementary to the respective base sequences to which the first primers hybridize, and the third primers do not comprise the base sequence which hybridizes to the second primer or to the base sequence complementary to the second primer.

4. The method according to claim 3, wherein, in the reaction solution, the abundance of the third primers is, by molar ratio, 0.25 to 4 times the abundance of the first primers.

5. The method according to claim 1, wherein, in the reaction solution, the abundance of the second primer is, by molar ratio, 1 to 400 times the abundance of each of the primers contained in the first primer set.

6. The method according to claim 1, wherein the reaction solution further comprises at least two detection probes that respectively recognize each of the at least two types of amplification product.

7. The method according to claim 1, wherein the first primers comprise at least one selected from the group consisting of bases that are mismatched, and bases that are degenerate, with respect to the base sequence of a region to be amplified.

8. The method according to claim 1, wherein the second primer has a higher Tm value than the first primers.

9. The method according to claim 1, wherein the second primer further comprises an additional base sequence that is different from the base sequence which hybridizes to the second primer or to the base sequence complementary to the second primer.

10. The method according to claim 1, wherein at least one of the at least two genes is a reference gene whose abundance in the subject sample is known in advance and at least one other gene of the at least two genes is a target gene whose abundance in the nucleic acids contained in the subject sample is to be measured.

11. The method according to claim 10, comprising determining the abundance of the target gene in the nucleic acids contained in the subject sample by comparing the detection signal of an amplification product derived from the reference gene with a detection signal of an amplification product derived from the target gene.

12. The method according to claim 1, wherein at least one of the at least two genes is a gene region located on the 5'-side upstream of a fusion point of a fusion gene and at least one other gene of the at least two genes is a gene region located on the 3'-side downstream of the fusion point of the fusion gene.

13. The method according to claim 12, further comprising detecting the presence of the fusion gene in the sample by comparing the detection signal of an amplification product derived from the gene region on the 5'-side and the detection signal of an amplification product derived from the gene region on the 3'-side.

14. The method according to claim 1, wherein the abundances of the at least two genes are determined by Tm analysis of at least two detection signals corresponding to the respective genes.

15. The method according to claim 1, wherein the signals that are used to determine the abundances of the at least two genes are obtained in terms of absorbance or fluorescence values measured at the same wavelength.

16. The method according to claim 14, wherein the abundances in the nucleic acids contained in the subject sample are determined by areal analysis of results from Tm analysis.

17. The method according to claim 1, wherein the molar ratio of the second primer in the reaction solution is from 4 to 20 times larger with respect to that of the first primer having the largest molar ratio among the first primers in the reaction solution.

18. The method according to claim 1, wherein the abundance of the genes in the nucleic acids are copy numbers of a gene in a genome DNA.

19. The method according to claim 6, wherein the two detection probes are labeled with the same fluorescent dye.

20. The method according to claim 19, wherein the detected signals in the determining step correspond to at least two changes in fluorescence intensity observed during dissociation of the at least two types of amplification product and the at least two detection probes corresponding to the amplification products.

21. The method according to claim 20, wherein the determining step comprises measuring the at least two changes in fluorescence intensity at the same wavelength, performing Tm analysis of the signals, and performing areal analysis of results from the Tm analysis.

22. A method of measuring copy numbers of a gene in a genomic DNA, the method comprising:
(1) obtaining at least two amplification products,
  by amplifying nucleic acids encoding the at least two genes contained in a subject sample in one reaction solution comprising (i) at least two detection probes that respectively recognize each of the at least two types of amplification products and are labeled with the same fluorescent dye, (ii) a second primer, and (iii) a first primer set, which includes at least two first primers, each of which comprises (a) a base sequence which hybridizes to the second primer or to the base sequence complementary to the second primer and (b) a sequence corresponding to each of the at least two genes,
  wherein the molar ratio of the second primer in the reaction solution is from 4 to 20 times larger with respect to that of the first primer having the largest molar ratio among the first primers in the reaction solution; and
(2) measuring signals corresponding to at least two changes in fluorescence intensity observed during dissociation of the at least two types of amplification products and the at least two detection probes corresponding to the respective amplification products, wherein the at least two changes are measured at the same wavelength,
(3) performing Tm analysis of the fluorescence intensity, and areal analysis of results from the Tm analysis,
(4) calculating the copy numbers of the at least two genes based on detected signals corresponding to the copy numbers of the at least two types of amplification product.

23. The method according to claim 1, wherein each of the first primers comprise the base sequence of the second primer.

24. The method according to claim 22, wherein each of the first primers comprise the base sequence of the second primer.

* * * * *